(12) United States Patent
Boynton et al.

(10) Patent No.: US 7,586,023 B1
(45) Date of Patent: *Sep. 8, 2009

(54) METHODS OF CONFERRING PPO-INHIBITING HERBICIDE RESISTANCE TO PLANTS BY GENE MANIPULATION

(75) Inventors: John E. Boynton, Durham, NC (US); Nicholas W. Gillham, Durham, NC (US); Barbara L. Randolph-Anderson, Mebane, NC (US); Fumiharu Ishige, Toyonaka (JP); Ryo Sato, Funabashi (JP)

(73) Assignees: Sumitomo Chemical Company, Limited, Osaka (JP); Duke University, Durham ( * ) Notice: Subject to any disclaimer, the term of this patent is extended or adjusted under 35 U.S.C. 154(b) by 0 days.

This patent is subject to a terminal disclaimer.

(21) Appl. No.: 09/331,723

(22) PCT Filed: Dec. 27, 1996

(86) PCT No.: PCT/US96/20415

§ 371 (c)(1),
(2), (4) Date: Aug. 18, 1999

(87) PCT Pub. No.: WO98/29554

PCT Pub. Date: Jul. 9, 1998

(51) Int. Cl.
*C12N 5/10* (2006.01)
*C12N 15/82* (2006.01)
*C07H 21/04* (2006.01)

(52) U.S. Cl. .................... 800/278; 435/320.1; 435/468; 536/23.6; 800/296

(58) Field of Classification Search ................ 435/69.1, 435/320.1, 410, 418, 419, 468; 536/23.6; 800/278, 295, 298, 300
See application file for complete search history.

(56) References Cited

U.S. PATENT DOCUMENTS

| 5,767,373 | A | | 6/1998 | Ward et al. ................. 800/278 |
| 5,939,602 | A | * | 8/1999 | Volrath et al. .............. 800/300 |
| 6,160,206 | A | * | 12/2000 | Sato et al. .................. 800/300 |

FOREIGN PATENT DOCUMENTS

| CA | 2167228 | | 4/1997 |
| WO | 95 34659 A | | 12/1995 |
| WO | WO-9534659 | * | 12/1995 |
| WO | 97 04088 A | | 2/1997 |
| WO | WO9704088 | | 2/1997 |
| WO | 97 04089 A | | 6/1997 |
| WO | 97 32011 A | | 9/1997 |

OTHER PUBLICATIONS

Barbara L. Randolph-Anderson et al., Isolation and characterization of a mutant protoporphyrinogen oxidase gene from chlamydomanas reinhardtii conferring resistance to porphyric herbicides, Plant Molecular Biology, 38, pp. 839-859.*
Saul Purton et al., Complementation of Chlamydomonas reinhardtii mutant using a genomic cosmid library, Plant Molecular Biology, 24, pp. 533-537.*
Puchta, H. Plant Mol. Biol., 2002, vol. 48, pp. 173-182.*
Terada et al., Nature Biotech., 2002, vol. 20, pp. 1030-1034.*
Li et al., Pest Manag. Sci., 2005, vol. 61, pp. 277-285.*
S.I. Narita et al., vol. 182, Dec. 5, 1996, pp. 169-175.
M. Kataoka et al., Journal of Pesticide Science, vol. 15, No. 3, Aug. 1990, pp. 449-451.
H. Oshio et al., Journal of Biosciences, vol. 48, No. 3/4, 1993, pp. 339-344.
R. Sato et al., ACS Symposium Series, vol. 559, 1995, pp. 91-104.

* cited by examiner

*Primary Examiner*—Ashwin Mehta
(74) *Attorney, Agent, or Firm*—Birch, Stewart, Kolasch & Birch, LLP

(57) ABSTRACT

The present invention provides methods to confer resistance to protoporphyrinogen-inhibiting herbicides onto crop plants. Resistance is conferred by genetically engineering the plants to express cloned DNA encoding a protoporphyrinogen oxidase resistant to porphyric herbicides. If such resistant crop plants are cultivated, utilization of these herbicides on fields of these crop plants becomes feasible. This should allow for simpler and more effective weed management, and increase the value of these herbicides for agricultural use. Furthermore, the present invention provides plants, algae, plant cells, and algal cells which have been made resistant to protoporphyrinogen oxidase-inhibiting herbicides by the subject methods using a herbicide-resistant protoporphyrinogen oxidase gene that has been prepared by genetic engineering methods. In addition, the present invention provides methods to evaluate the inhibitory effects of test compounds on protoporphyrinogen oxidase activity, as well as methods to identify protoporphyrinogen oxidase inhibitors among test compounds. Preferred cloned DNA fragments encoding protoporphyrinogen oxidase enzymes resistant to porphyric herbicides are also described.

15 Claims, 3 Drawing Sheets

METHODS OF CONFERRING PPO-INHIBITING HERBICIDE RESISTANCE TO PLANTS BY GENE MANIPULATION

This application is the national phase under 35 U.S.C. §371 of prior PCT International Application No. PCT/US96/20415 which has an International filing date of Dec. 27, 1996 which designated the United States of America.

BACKGROUND OF THE INVENTION

1. Field of the Invention

The present invention relates to DNA fragments that confer resistance to protoporphyrinogen oxidase (PPO; EC 1.3.3.4)—inhibiting herbicides onto plants, plasmids and microorganisms that contain these DNA fragments. The present invention also relates to methods of conferring resistance onto plants and plant cells by using genetically engineered DNA fragments that encode PPO. Other aspects of the present invention are plants and plant cells onto which have been conferred resistance to PPO-inhibiting herbicides. Another aspect of the present invention relates to a method for evaluating the inhibitory effects of compounds on PPO activity utilizing microbial systems differing only by the presence of genes encoding PPO resistant or sensitive to said compounds.

2. Description of Related Art

A group of widely-known compounds used as active ingredients of some varieties of commercially- and otherwise-available herbicides exhibit herbicidal activity in the presence of light, but exhibit no herbicidal activity in darkness. This has led to their common designation as light-dependent herbicides. It has recently been shown that these herbicides induce high levels of porphyrin accumulation in plants and algae, and thus they are now designated as "porphyrin-accumulating type herbicides" [Zoku, Iyakuhin-no-Kaihatsu, (translation: "*The Development of Medical Drug Products*; continuation") vol. 18; *Development of Agricultural Chemicals II*, chapter 16, section 16-1, 1993, Iwamura et al., eds., Hirokawa Shoten, Tokyo ) or simply "porphyric herbicides". It was reported by Matringe et al., (*Biochem J.* 260:231 (1989) and (*FEBS Lett.* 245: 35 (1989)) that porphyrin-accumulating type herbicides inhibit isolated protoporphyrinogen oxidase. Thus porphyria herbicides are also called PPO-inhibiting herbicides. Protoporphyrinogen oxidase is commonly found in microorganisms such as bacteria and yeast, plants including algae and animals. This enzyme catalyzes the last oxidation step which is common in both the heme and the chlorophyll biosynthesis pathways, namely the oxidation of protoporphyrinogen IX to protoporphyrin IX (Matringe et al., *Biochem J.* 260: 231 (1989)).

Bacterial PPOs are thought to be localized in the cytoplasm and the genes encoding bacterial PPOs have been isolated from *Escherichia coli* (Gen Bank accession X68660: ECHEMGA; Sasarman et al., *Can. J. Microbiol.* 39: 1155 (1993)) and *Bacillus subtilis* (Gen Bank accession M97208: BACHEMEHY, Daily et al., *J. Biol. Chem.* 269: 813 (1994)). Mouse (Gen Bank accession U25114:MMU25114), human (Gen Bank accession D38537:HUMPOX and U26446: HSU26446) and yeast (Ward & Volrath, WO 95/34659, 1996) genes encoding mitochondrial PPO have been isolated. Genes encoding chloroplast PPO have also been isolated from *Arabidopsis thaliana* and maize (Ward & Volrath, WO 95/34659, 1996).

Like higher plants, the unicellular green alga *Chlamydomonas reinhardtii* is highly sensitive to PPO-inhibiting herbicides. However, a mutant strain designated RS-3 (Kataoka et al., *J. Pesticide Sci.* 15: 449 (1990)) shows resistance specifically to PPO inhibitors. This resistance results from a single dominant nuclear mutation (Sato et al., *Porphyric Pesticides: Chemistry, Toxicology and Pharmaceutical Applications*, Duke & Rebeiz eds., ACS symposium series 559, pp. 91-104, c. 1994 by the American Chemical Society, Washington D.C.). Furthermore, PPO activity in isolated chloroplast fragments from the RS-3 mutant is significantly less sensitive to PPO inhibitors than similar chloroplast fragments from wild type *C. reinhardtii* (Shibata et al., *Research in Photosynthesis* Murata ed., Vol. III, pp. 567-570, c. 1993 by Kluwer 5 Academic Publishers, Dordrecht, Netherlands).

Since most crop plants do not exhibit resistance to PPO-inhibiting herbicides, these compounds cannot be used on farmland when such crops are under cultivation. If it were possible to develop crop plants resistant to PPO-inhibiting herbicides, such herbicides could be used for weed control during the growing season. This would make crop management easier, and increase the value of these herbicides in agricultural applications. For this reason, it is desirable to develop a method for conferring resistance to PPO-inhibiting herbicides or porphyrin-accumulating herbicides upon crop plants.

SUMMARY OF THE INVENTION

With this goal in mind, the present inventors have investigated a mutant strain, designated RS-3, of the unicellular green alga *Chlamydomonas reinhardtii* which shows specific resistance to PPO-inhibiting herbicides. The present inventors therefore isolated clones that contain a gene responsible for resistance to PPO-inhibiting herbicides from a genomic DNA library constructed from total nuclear DNA of the RS-3 mutant and succeeded in isolating DNA fragments which confer PPO-inhibiting herbicide resistance to plant or algal cells. The inventors further demonstrated that these DNA fragments contain PPO gene sequences and that the DNA fragments from the RS-3 mutant have a single base pair substitution leading to an amino acid substitution within a highly conserved domain of the plant PPO protein. Thus, the inventors were able to establish methods that will confer PPO-inhibiting herbicide resistance onto plants or algae by introducing a genetically engineered PPO gene which results in a specific amino acid substitution in the PPO enzyme.

An objective of the present invention is to provide a method of conferring resistance to PPO-inhibiting herbicide upon plants or plant cells, including algae, comprising introducing a DNA fragment or biologically functional equivalent thereof, or a plasmid containing the DNA fragment, into plants or plant cells, including algae, wherein said DNA fragment or said biologically functional equivalent is expressed and has the following characteristics:

(1) said DNA fragment encodes a protein or a part of a protein having plant PPO activity, (2) said DNA fragment has a homologous sequence that can be detected and isolated by DNA-DNA or DNA-RNA hybridization methods, with respect to a nucleic acid encoding an amino acid sequence shown in SEQ. ID. No.: 1 or SEQ. ID. No.: 2 or SEQ. ID. No.: 3, and encodes a protein in which an amino acid corresponding to Val13 of SEQ. ID. No.: 1 or SEQ. ID. No.: 2 or SEQ. ID. No.: 3 is artificially substituted with another amino acid by a genetic engineering method, and (3) said DNA fragment has the ability to confer resistance to PPO-inhibiting herbicides in plant or algal cells when expressed therein.

Another objective of the present invention is to provide a plant or plant cells upon which resistance is conferred by the method described above.

A further objective of the present invention is to provide a method for selecting plant cells upon which resistance to PPO-inhibiting herbicides is conferred, comprising treating a population of plant cells upon which resistance to PPO-inhibiting herbicide is conferred by the present methods with a PPO-inhibiting herbicide in an amount which normally inhibits growth of sensitive plant cells.

A still further objective of the invention is to provide a method of controlling plants sensitive to PPO-inhibiting herbicides in a field of crop plants upon which resistance to PPO-inhibiting herbicides is conferred by the methods described herein, comprising applying PPO-inhibiting herbicide in an effective amount to inhibit growth of said PPO-inhibiting herbicide-sensitive plants.

A still further objective of the invention is to provide a DNA fragment or biologically functional equivalent thereof which has the following characteristics:

(1) said DNA fragment encodes a protein or a part of the protein having plant PPO activity.

(2) said DNA fragment has a homologous sequence that can be detected and isolated by DNA-DNA or DNA-RNA hybridization methods, with respect to a nucleic acid encoding an amino acid sequence shown in SEQ. ID. No.: 1 or SEQ. ID. No.: 2 or SEQ. ID. No.: 3.

(3) said DNA fragment encodes a protein in which an amino acid corresponding to Val13 of SEQ. ID. No.: 1 or SEQ. ID. No.: 2 or SEQ. ID. No.: 3 is artificially substituted by a different amino acid by a genetic engineering method, and (4) said DNA fragment has the ability to confer resistance to PPO-inhibiting herbicides in plant or algal cells when expressed therein.

Still further objectives of the invention are to provide a plasmid comprising the DNA fragment or biologically functional equivalent thereof described above, and a microorganism harboring the plasmid.

Still further objectives of the invention are to provide a method for evaluating the inhibitory effect of a test compound on PPO, comprising (a) culturing a sensitive microorganism containing a gene encoding a protein with PPO activity sensitive to PPO inhibitors and a resistant transformant microorganism in the presence of a test compound. In this method, the resistant transformant microorganism differs from the said sensitive microorganism only by the presence of a gene encoding a protein with PPO activity resistant to PPO inhibitors in which the amino acid corresponding to Val13 of SEQ. ID. No.: 1 or SEQ. ID. No.: 2 or SEQ. ID. No.: 3 is replaced with another amino acid artificially by a genetic engineering method, and (b) evaluating the growth of both sensitive and resistant microorganisms to determine the inhibitory effect of the test compound on PPO. Said method includes:

(1) a method of selecting a PPO inhibitor, comprising (a) culturing in the presence of a test compound a sensitive microorganism having a gene encoding a protein with PPO activity sensitive to PPO inhibitors and a microorganism differing from said microorganism by the presence of a gene encoding a protein with PPO activity resistant to PPO inhibitors in which an amino acid corresponding to Val13 of SEQ. ID. No.: 1 or SEQ. ID. No.: 2 or SEQ. ID. No.: 3 is artificially replaced with another amino acid by a genetic engineering method, and (b) identifying compounds which inhibit growth of only the sensitive microorganisms at a particular dosage where resistant microorganisms will grow; and (2) a method of selecting a compound that does not inhibit PPO, comprising culturing a sensitive microorganism having a gene encoding a protein having PPO activity sensitive to PPO inhibitors and a resistant transformant microorganism differing only from said sensitive microorganism by the presence of a gene encoding a protein with PPO activity resistant to PPO inhibitors and having an amino acid substitution at the position corresponding to Val13 of SEQ. ID. No.: 1 or SEQ. ID. No.: 2 or SEQ. ID. No.: 3 introduced by a genetic engineering method, and (b) identifying the compounds which inhibit growth of both sensitive and resistant microorganisms.

BRIEF DESCRIPTION OF THE DRAWINGS

FIG. 1(a): 2.6 kb DNA fragment designated as Xho/PmaC2.6;

FIG. 1(b): 3.4 kb DNA fragment designated as Xho3.4;

FIG. 1(c): 10.0 kb DNA fragment designated as HindI0.0;

FIG. 1(d): 13.8 kb DNA fragment designated as Eco13.8;

FIG. 1(e): an approximately 40.4 kb DNA fragment possessed by the cosmid clone 2955 (Cos2955) from the RS-3 mutant.

DETAILED DESCRIPTION OF THE INVENTION

Figure 1:
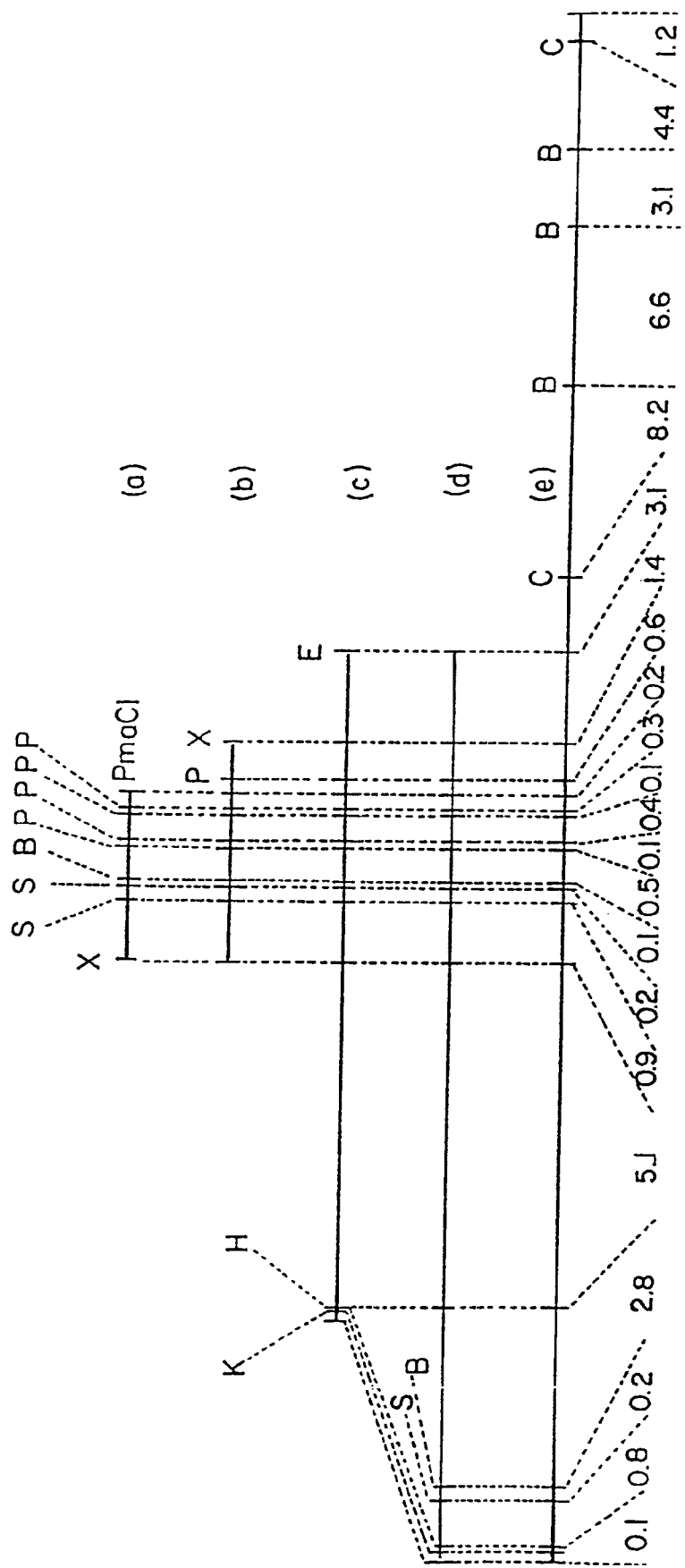
FIG. 1(a)-1(e) shows restriction site maps of cloned DNA fragments which confer resistance to porphyrin-accumulating type herbicides. The sizes of the fragments are indicated by the numbers (kb) in FIG. 1(e). XhoI and HindIII sites are shown in FIG. 1(a)-FIG. 1(d). PstI and PmaCI sites are shown only in FIG. 1(a). Abbreviations: B, BamHI; S, SalI; P, PstI; X, XhoI; E, EcoRI; H, HindIII; K,KpnI; C, ClaI.

With regard to the terminology used herein, the term "DNA fragments" refers not only to the DNA fragments that may be used in the subject method of conferring PPO-inhibiting herbicide resistance, but also to degenerate isomers and genetically equivalent modified forms of these fragments. "Degenerate isomers" is taken here to mean isomers whose nucleotide base sequence is degenerately related to the original fragments; that is, all nucleic acid fragments including the corresponding mRNA or corresponding cDNA, or corresponding PCR product that encode the same amino acid sequence as the original fragments. "Genetically equivalent modified forms" is taken here to mean DNA fragments that may have undergone base changes, additions, or deletions, but which essentially contain the same inherent genetic information as the original fragments; i.e., the ability to confer resistance to PPO-inhibiting herbicides onto plants and plant cells.

Plants used in, or themselves representing, embodiments of the invention can be either algae, monocots or dicots. Genetic engineering methods applicable to these types of plants are known in the art.

The phrase "protoporphyrinogen oxidase-inhibiting herbicides" or "PPO-inhibiting herbicides" refers to "porphyrin-accumulating type" or "porphyric herbicides", i.e., compounds that induce the accumulation of high levels of porphyrins in plants to which they have been applied and which kill sensitive plants in the presence of light, including compounds that inhibit protoporphyrinogen oxidase (PPO) activity isolated from susceptible plants in vitro. The herbicides that inhibit PPO include many different structural classes of molecules (Duke et al., *Weed Sci.* 39: 465 (1991); Nandihali et al., *Pesticide Biochem. Physiol.* 43: 193 (1992), Matringe et al., *FEBS Lett.* 245: 35 (1989); Yanase & Andoh, *Pesticide Biochem. Physiol.* 35: 70 (1989); Anderson et al., ACS Symposium Series, Vol. 559, *Porphyric Pesticides*, S. O. Duke and C. A. Rebeiz eds., p 18-34 (1994)). These herbicides include, for example, oxadiazon, [N-(4-chloro-2-fluoro-5-propargyloxy)phenyl-]3,4,5,6-tetrahydrophthalimide (referred to below as compound A), and the diphenyl ether herbicides such as acifluorfen, lactofen, fomesafen, oxyfluorfen. Also of significance are the class of herbicides having the general formula X-Q, wherein Q is

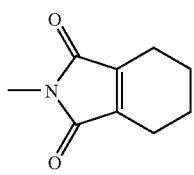

(Formula 1)

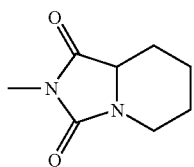

(Formula 2)

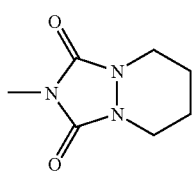

(Formula 3)

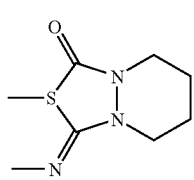

(Formula 4)

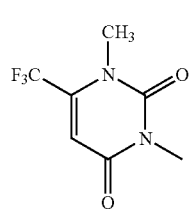

(Formula 5)

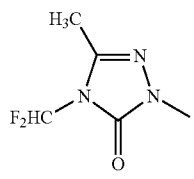

(Formula 6)

-continued

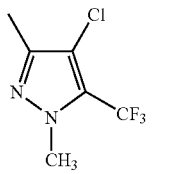

(Formula 7)

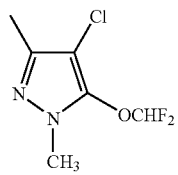

(Formula 8)

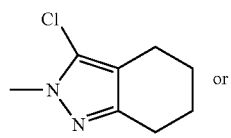

or (Formula 9)

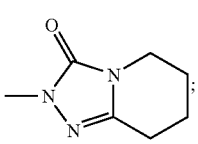

;

(Formula 10)

and X equals

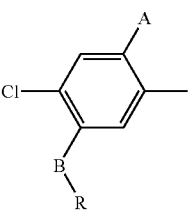

(Formula 11)

wherein

B=O, S

R=$C_1$-$C_8$ alkyl,
  $C_3$-$C_8$ alkenyl,
  $C_3$-$C_8$ alkynyl (Formula 12)

wherein

A=H, halogen

B=O, S

R'=H, CH₃

R=$C_1$-$C_8$ alkyl
$C_3$-$C_8$ alkenyl
$C_3$-$C_8$ alkynyl

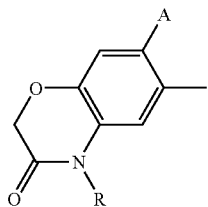
(Formula 13)

wherein

A=H, halogen

R=$C_1$-$C_8$ alkyl,
$C_3$-$C_8$ alkenyl,
$C_3$-$C_8$ alkynyl

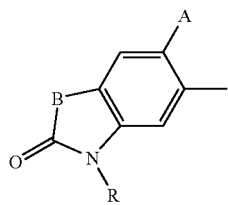
(Formula 14)

wherein

A=H, halogen

B=O, S

R=$C_1$-$C_8$ alkyl,
$C_3$-$C_8$ alkenyl,
$C_3$-$C_8$ alkynyl

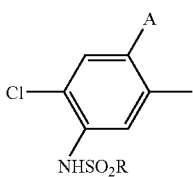
(Formula 15)

wherein

A=H, halogen

R=$C_1$-$C_8$ alkyl,
$C_3$-$C_8$ alkenyl,
$C_3$-$C_8$ alkynyl

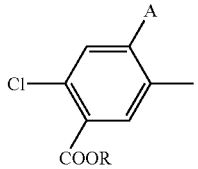
(Formula 16)

wherein

A=H, halogen

R=$C_1$-$C_8$ alkyl,
$C_3$-$C_8$ alkenyl,
$C_3$-$C_8$ alkynyl

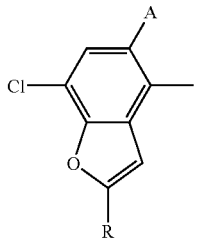
(Formula 17)

wherein

A=H, halogen

R=$C_1$-$C_8$ alkyl,
$C_3$-$C_8$ alkenyl,
$C_3$-$C_8$ alkynyl

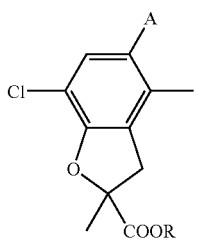
(Formula 18)

wherein

A=H, halogen

R=$C_1$-$C_8$ alkyl,
$C_3$-$C_8$ alkenyl,
$C_3$-$C_8$ alkynyl

Examples of herbicides of particular interest are (Formula 19)

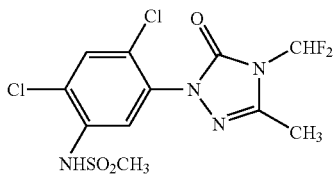

(Formula 20)

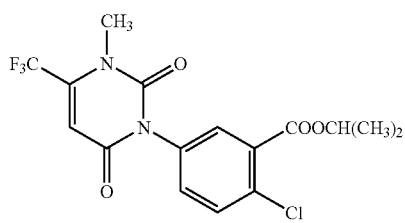

(Formula 21)

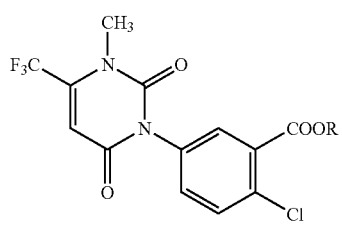

wherein

R=($C_2$-$C_5$ alkenyloxy) $C_1$-$C_4$ alkyl (Formula 22)

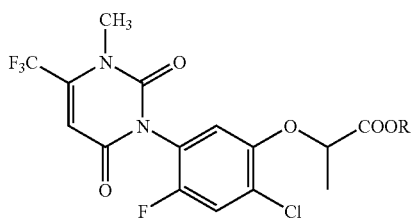

wherein

R=$C_1$-$C_1$ alkyl,
$C_3$-$C_8$ alkenyl,
$C_3$-$C_8$ alkynyl and (Formula 23)

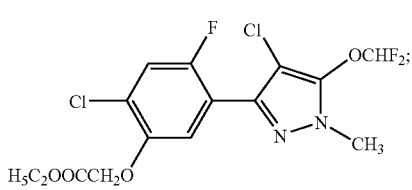

as well as the following:
pentyl[2-chloro-5-(cyclohex-1-ene-1,2-dicarboximido)-4-fluorophenoxy]acetate,
7-fluoro-6-[(3,4,5,6,-tetrahydro)phthalimido]-4-(2-propynyl)-1,4-benzoxazin-3(2H)-one,
6-[(3,4,5,6-tetrahydro)phthalimido]-4-(2-propynyl)-1,4-benzoxazin-3(2H)-one,
2-[7-fluoro-3-oxo-4-(2-propynyl)-3,4-dihydro-2H-1,4-benzoxazin-6-yl]perhydroimidazo[1,5-a]pyridine-1,3-dione,
2-[(4-chloro-2-fluoro-5-propargyloxy)phenyl] perhydro-1H-1,2,4-triazolo-[1,2-a]pyridazine-1,3-dione,
2-[7-fluoro-3-oxo-4-(2-propynyl)-3,4-dihydro-2H-1,4-benzoxazin-6-yl]5,6,7,8-1,2,4-triazolo[4,3-a]pyridine-3H-one,
2-[3-oxo-4-(2-propynyl)-3,4-dihydro-2H-1,4-benzoxazin-6-yl]-1-methyl-6-trifluoromethyl-2,4(1H,3H)-pyrimidinedione,
2-[6-fluoro-2-oxo-3-(2-propynyl)-2,3-dihydrobenzthiazol-5-yl]-3,4,5,6-tetrahydrophthalimide,
1-amino-2-[3-oxo-4-(2-propynyl)-3,4-dihydro-2H-1,4-benzoxazin-6-yl]-6-tri-fluoromethyl-2,4(1H,3H)-pyrimidinedione, and analogs of these compounds.

The DNA fragments or their equivalents that may be used in the subject method of conferring PPO-inhibiting herbicide resistance have the following characteristics: (1) said DNA fragments encode a protein or part of a protein having plant PPO activity; (2) said DNA fragments have a sequence, homologous with nucleic acids encoding the amino acid sequence specified by SEQ. ID. No.:1 or SEQ. ID. No.: 2 or SEQ. ID. No.: 3, that can be isolated by conventional DNA-DNA or DNA-RNA hybridization methods. Said DNA fragments encode a protein having a homologous amino acid sequence specified by SEQ. ID. No.: 1 or SEQ. ID. No.: 2 or SEQ. ID. No.: 3 with an amino acid substitution at the position corresponding to Val13 of SEQ. ID. No.: 1 or SEQ. ID. No.: 2 or SEQ. ID. No.: 3 by, for example, methionine; and (3) said DNA fragments have the ability to confer resistance to PPO-inhibiting herbicides onto plants and plant cells.

The DNA fragments that may be used in the subject method for conferring PPO-inhibiting herbicide resistance may be constructed by the artificial synthesis of their nucleotide sequences according to, for example, SEQ. ID. No. 4 or SEQ. ID. No.: 5 or SEQ. ID. No.: 6. However, they are more typically prepared by the following procedures: (1) isolating DNA fragments that encode a protein or part of a protein having PPO activity and conferring PPO-inhibiting herbicide resistance to sensitive wild type cells by known transformation methods using donor DNA from a mutant strain of the unicellular green alga *Chlamydomonas reinhardtii*, designated RS-3, that is resistant to PPO-inhibiting herbicides; (2) identifying the mutation found in the DNA fragments isolated from the said mutant as above; (3) isolating DNA fragments that encode a protein or part of a protein having PPO activity (referred to as a "PPO gene") by known methods including those described in this invention and identifying the nucleotide sequence domain of said PPO gene corresponding to SEQ. ID. No.: 4 that contains the PPO-inhibiting herbicide resistance mutation of the RS-3 strain; (4) introducing a specific base pair substitution into said PPO gene, which results in an amino acid alteration of the encoded protein equivalent to that found in the PPO-inhibiting herbicide resistance mutation of the RS-3 strain, by known molecular biology techniques such as site-directed mutagenesis. Alternatively, DNA fragments having domains homologous to nucleic acids encoding the amino acid SEQ. ID. No.: 1 or SEQ. ID. No.: 2 or SEQ. ID. No.: 3 (for example, SEQ. ID. No.: 4 or SEQ. ID. No.: 5 or SEQ. ID. No.: 6) may be isolated by known DNA-DNA, DNA-RNA hybridization methods or known PCR methods. A base pair substitution which results in the same amino acid alteration as that found in the PPO-inhibiting herbicide resistance mutation of the RS-3 strain may then be introduced into the DNA fragment as described above. In some embodiments, the homologous DNA domain will have only one or two nucleotides differing from a sequence selected from SEQ. ID. No.: 4 or SEQ. ID. No.: 5 or SEQ. ID. No.: 6. In some embodiments of the invention, the nucleotide sequence of PPO gene is identical to the sequence of the PPO gene of wild-type C. rheinhardtii, except that one to six nucleotides in the portion of the sequence represented by SEQ. ID. No.: 4 are different. The differences will preferably encode mutations of one to three, most preferably one or two changes to the amino acid sequence of SEQ. ID. No.: 1.

In some embodiments of the invention, the nucleotide sequence of PPO gene is identical to the sequence of the PPO gene of wild-type A. thaliana, except that one to six nucleotides in the portion of the sequence represented by SEQ. ID. No.: 5 are different. The differences will preferably encode mutations of one to three, most preferably one or two changes to the amino acid sequence of SEQ. ID. No.: 2.

In some embodiments of the invention, the nucleotide sequence of PPO gene is identical to the sequence of the PPO gene of wild-type Zea mays, except that one to six nucleotides in the portion of the sequence represented by SEQ. ID. No.: 6 are different. The differences will preferably encode mutations of one to three, most preferably one or two changes to the amino acid sequence of SEQ. ID. No.: 3.

The mutant strain RS-3 is stored at the Chlamydomonas Genetics Center (address: DCMB Group, Department of Botany, Box 91000, Duke University, Durham, N.C. 27708-1000, USA) under the entry number GB-2674. Thus, the mutant strain RS-3 is publicly available for distribution by permission. A 2.6 kb DNA fragment (SEQ. ID. No.: 10, (a) in FIG. 1) containing the nucleic acid SEQ. ID. No.: 4 can be easily prepared from a plasmid (FIG. 2) having a 13.8 kb DNA fragment ((d) in FIG. 1) containing the 2.6 kb DNA fragment by digesting the plasmid with the restriction enzyme Xho I, isolating a 3.4 kb DNA fragment ((b) in FIG. 1) by agarose gel electrophoresis, digesting the 3.4 kb fragment with the restriction enzyme PmaCI, and separating the digest by agarose gel electrophoresis. As will be described below, a host microorganism containing the plasmid pBS-Eco 13.8 is also on deposit under the terms of the Budapest Treaty, and is thus freely available. The plasmid hosted by the microorganism can be readily extracted using conventional techniques.

The nucleic acid sequences shown by the SEQ. ID. No.:4 or SEQ. ID. No.: 5 or SEQ. ID. No.: 6 are parts of a sequence of the gene encoding a PPO protein which is thought to be localized in chloroplasts from Chlamydomonas reinhardtii, Arabidopsis thaliana, and maize, respectively. These sequences represent an amino acid domain highly homologous among plant chloroplast PPO enzymes. Therefore, it is feasible to obtain DNA fragments that can be modified to confer resistance to PPO-inhibiting herbicides and used in the subject method by isolating DNA fragments encoding a protein having PPO activity, and identifying the domain of the fragments with homology to SEQ. ID. No.: 4 or SEQ. ID. No.: 5 or SEQ. ID. No.: 6. A specific base pair substitution can then be introduced, for example G37 to A37 of SEQ. ID. No.: 4 (GTG to ATG), which results in an amino acid substitution, for example from Val to Met at the position of Val13 of the amino acid SEQ. ID. No.: 1 or SEQ. ID. No.: 2 or SEQ. ID. No.: 3.

Said DNA fragments encoding a protein having PPO activity can be obtained, for example, by the following procedures: (1) preparing a cDNA library from the plant material of interest; (2) identifying clones which are able to supply PPO activity to a mutant host-organism deficient in this activity. Suitable host organisms which can be used to screen the aforementioned cDNA expression libraries, and for which mutants deficient in PPO activity are either available or can be readily generated, include, but are not limited to, E. coli (Sasarman et al., J. Gen. Microbiol. 113: 297 (1979)), Salmonella typhimurium (Xu et al., J. Bacteriol. 174: 3953 (1992)), and Saccharomyces cerevisiae (Camadro et al., Biochem. Biophys. Res. Comm. 106: 724 (1982)). The DNA fragments thus obtained may be introduced by any known transformation method to confer PPO-inhibiting herbicide resistance to the recipient plant cells when expressed. Said DNA fragments may be introduced into plant or algal cells by themselves, or in the form of chimeric gene constructs comprising the DNA fragment containing the herbicide-resistant PPO coding sequence and a promoter, especially a promoter that is active in plants, operably linked to the PPO coding sequence and/or a signal sequence operably linked to this sequence, wherein said signal sequence is capable of targeting the protein encoded by the DNA fragment to the chloroplast. Alternatively, said DNA fragments or chimeric gene constructs can be introduced into plant cells as a part of a plasmid or other vector.

Plant cells resistant to PPO-inhibiting herbicides due to the presence of the altered PPO coding sequence may be isolated by growing the population of the plant cells on media containing an amount of a PPO-inhibiting herbicide which normally inhibits growth of the untransformed plant cells. When said DNA fragment or chimeric gene containing the DNA fragment is linked to a marker selective for transformation, transformed cells may first be isolated by utilizing the selectable marker. The PPO-inhibiting herbicide-resistant cells may be then be isolated from the transformed cells as described above.

The PPO-inhibiting herbicide-resistant cells thus obtained may be grown by known plant cell and tissue culture methods. PPO-inhibiting herbicide-resistant plants may be obtained by regenerating plants from plant cell and tissue cultures thus obtained, again using known methods.

Further scope of the applicability of the present invention will become apparent from the examples provided below. It should be understood, however, that the following examples, while indicating preferred embodiments of the invention, are given by way of illustration only. Various changes and modifications of the invention will become apparent to those skilled in the art from this detailed description and such modifications should be considered to fall within the scope of the invention defined by the claims.

General Methods

Plant tissue including leaves and stems of a species of interest such as Arabidopsis thaliana, obtained from stock centers, such as Arabidopsis Biological Resource Center (ABRC), 1735 Neil Avenue, Columbus, Ohio 43210, USA, or the Nottingham Arabidopsis Stock Center (NASC), Department of Life Science, University of Nottingham, University Park, Nottingham, NG72RD, United Kingdom, or the Sendai Arabidopsis Seed Stock Center, Department of Biology, Miyagi College of Education, Aoba-yama, Sendai 980, Japan, is frozen in liquid nitrogen, then homogenized mechanically by a Waring blender or with a mortar and pestle. After vaporizing the liquid nitrogen, RNA can be extracted from the homogenate. A commercially available kit for RNA extraction may be used in this procedure. Total RNA is recovered from the extract by the conventional ethanol precipitation method. Then, the poly-A RNA fraction is separated from the total RNA thus obtained by conventional methods such as a commercially available oligo dT column. cDNA is synthesized from the poly-A RNA fraction thus obtained, according to a standard method. A commercially available kit for cDNA synthesis may be used for this procedure. cDNA thus obtained is cloned-into an expression vector, preferably a λ phage vector such as λgt 11, digested with an appropriate restriction enzyme such as Eco RI, after ligating an appropriate adaptor (e.g. an Eco RI adaptor) to the cDNA with T4 DNA ligase. A commercially available kit for preparing cDNA libraries can be used for this procedure as well as for in vitro packaging and transduction.

After amplifying the cDNA library thus obtained, a mutant strain of *E. coli* (e.g. strain SASX38, Sasarman et al. *J. Gen. Microbiol.* 113: 297 (1979)) deleted with respect to its PPO gene (hemG locus) which is described, for example, by Miyamoto et al. (*J. Mol. Biol.* 219: 393 (1991)) and Nishimura et al., (*Gene* 133: 109 (1993)) is infected with the cDNA library, then plated onto appropriate agar medium plates such as LB plates and incubated for two days. The host cells show limited growth and form minute colonies on the agar plates because of the hemG-phenotype (lacking a PPO gene), while transformed cells expressing PPO activity from the cDNA, e.g. encoding *Arabidopsis* PPO, show faster growth and form relatively larger colonies on the agar plates than untransformed cells. By isolating these larger colonies, *E. coli* host cells harboring the cDNA encoding a plant PPO can be obtained.

Then, the vector containing the cloned DNA is recovered. For example, lambda phage are recovered from the lysed host cells which have been exposed to UV light. The recovered vectors are analyzed according to a conventional method, e.g. Watanabe & Sugiura, *Shokubutu Biotechnology Jikken Manual, cloning and sequencing* (Translation; *Manual for Plant Biotechnology Experiments, cloning and sequencing*) pp. 180-189, Nouson Bunka Sha (1989)), in order to isolate the clone possessing the longest insert as the positive cDNA clone.

The insert of the cDNA clone thus isolated is recovered from the vector and can be subcloned into a commercially available plasmid vector (for example pUC118 or pBluescript) according to standard methods (e.g. Short et al., *Nucleic Acids Research* 16: 7583 (1988)). A series of deletions of the insert thus re-cloned into the plasmid vector may be prepared according to a standard method (e.g. Vieira & Messing, *Methods in Enzymol.* 153: 3 (1987)). These clones containing the insert or part of the insert are used for the determination of the nucleotide sequence by the dideoxychain-termination method (e.g. Sanger et al., *Proc. Nat. Acad. Sci. U.S.A.* 74: 5463 (1977)). A commercially available kit may be used for this sequencing procedure.

The DNA fragments thus obtained, preferably part of the DNA fragment comprising the conserved domain of the PPO coding sequence such as SEQ. ID. Nos.: 4-6, can be used as probes for screening of a genomic DNA or cDNA library of interest, in order to isolate other DNA fragments encoding a protein or a part of a protein having PPO activity. Alternatively, the conserved domain of the PPO coding sequence such as SEQ. ID. Nos.: 4-6 may be amplified by known PCR methods e.g. (*PCR Protocols, a Guide to Methods and Applications*, Innis et al.,eds., c. 1990 by Academic Press, San Diego, Calif.), using appropriate primers and the PCR product corresponding to the conserved domain of the PPO coding sequence can be used for screening of a genomic DNA or cDNA library of interest, in order to isolate other DNA fragments encoding the entire protein or a part of the protein having PPO activity.

Alternatively, DNA fragments encoding a protein having PPO activity can also be isolated from mutant cells resistant to PPO-inhibiting herbicides using conventional genetic engineering protocols such as those described in *Molecular Cloning*, 2nd Edition, by Sambrook et al., c. 1989 by Cold Spring Harbor Publications, Cold Spring Harbor, N.Y. For example, genomic DNA can be extracted from the RS-3 mutant of unicellular green alga *Chlamydomonas reinhardtii*, in which herbicide resistance results from a mutation causing PPO to become herbicide-resistant, according to a protocol such as that described by E. H. Harris, *The Chlamydomonas Sourcebook*, pp. 610-613, c. 1989 by Academic Press, San Diego, Calif. Namely, *C. reinhardtii* cells are lysed and the DNA is extracted by treatment with protease and surface active agents such as SDS or Sarkosyl. Genomic DNA is subsequently extracted by conventional techniques involving centrifugation and phenol-chloroform extraction, etc. to remove proteins, after which the DNA is recovered by ethanol precipitation. The DNA thus obtained is further purified by sodium iodide-ethidium bromide density gradient centrifugation, and the lowermost, major band corresponding to nuclear genomic DNA is recovered. Nuclear genomic DNA thus obtained is partially digested using an appropriate restriction enzyme such as Sau3AI. Linkers or adaptors are attached to both ends of the DNA fragments thus obtained using T4 DNA ligase. If necessary, excess free linkers or adaptors can be removed by gel filtration, and the fragments can then be inserted into an appropriate commercially available cosmid vector or a phage vector derived from λ phage. Phage particles generated by an in vitro packaging procedure are transfected into *E. coli* and allowed to form colonies or plaques on solid media. An indexed genomic DNA library can be obtained by isolating and maintaining individual *E. coli* clones harboring hybrid cosmids (e.g. Zhang et al., *Plant Mol. Biol.* 24: 663 (1994)) or the library can be kept by conventional methods for isolating and maintaining *E. coli* clones or phage particles in a mixture.

Genomic clones containing gene sequences carrying the rs-3 mutation conferring resistance to PPO-inhibiting herbicides can be isolated from the genomic DNA library by screening the library with an oligonucleotide probe synthesized to correspond to the deduced amino acid sequence encoded by a PPO gene. This probe can be labeled with a radioisotope or fluorescent tag and used to identify genomic DNA clones containing the subject DNA fragments by colony hybridization (Sambrook et al., *Molecular Cloning*, 2nd. ed., p. 1.90, c. 1989 by Cold Spring Harbor Publications, Cold Spring Harbor, N.Y.). Alternatively, the genomic clones containing said DNA fragments could be screened by transforming a strain of *Chlamydomonas reinhardtii* sensitive to porphyric herbicides with the genomic DNA from the cosmid library using normal transformation techniques for this organism (e.g. Kindle, *Proc. Natl. Acad. Sci. U.S.A.* 87: 1228 (1990); Boynton & Gillham, *Methods In Enzymol., Recombinant DNA*, Part H, 217: 510, Wu, ed., c. 1993 by Academic Press, San Diego, Calif.) to isolate hybrid cosmids containing nuclear genomic DNA fragments capable of conferring resistance to porphyric herbicides. A restriction map of the hybrid cosmid clone identified by one of the aforementioned protocols can be determined using any one of several standard methods. Various restriction fragments are subcloned into the pBluescript vector, and subclones that conferred resistance to porphyric herbicides to normally sensitive *Chlamydomonas* strains are identified. In one example below, a 2.6 kb DNA fragment which encodes a part of PPO enzyme resistant to PPO-inhibiting herbicides and is capable of conferring resistance to PPO-inhibiting herbicides on sensitive wild type cells, and plasmids containing this DNA fragment are isolated. Using the subject DNA fragments and the subject plasmids as starting material, the nucleotide sequences of the DNA fragments are determined by the method of Maxam and Gilbert (*Proc. Natl. Acad. Sci. U.S.A.* 74: 560 (1977)) or by the method of Sanger (Sanger & Coulson (*J. Mol. Biol.* 94: 441 (1975); Sanger et al., *Proc. Natl. Acad. Sci. U.S.A.* 74: 5463 (1977)) or improved versions of this method.

The herbicide resistance mutation in the DNA fragment encoding a herbicide-resistant PPO enzyme thus obtained can be identified by determining the corresponding sequence of the sensitive wild type gene and comparing both sequences. The corresponding wild type gene can be isolated by several methods as described above. Alternatively, exon sequences of the genomic DNA fragment encoding a herbicide-resistant PPO gene thus obtained can be determined by comparing its sequence with known sequences of PPO genes whose protein products localize to the chloroplast. For example, the *Arabidopsis* and maize cDNA sequences encoding a protein having PPO activity and a chloroplast-targeting signal peptide can be used as known sequences. The exons can then be amplified from wild type genomic DNA by PCR methods developed for the high G+C content nuclear DNA of *Chlamydomonas reinhardtii* as described below. The wild type sequences of the amplified DNA fragments corresponding to the exons of interest can be determined with a commercially available kit for sequencing, such as the ds DNA Cycle Sequencing System (GIBCO BRL, Life Technologies, Inc).

Using standard transformation methods, the DNA fragment isolated from the RS-3 mutant can be shown to confer PPO herbicide resistance to sensitive cells. The DNA fragment can also be shown to encode a protein or a part of a protein having PPO activity which is supposed to localize in the chloroplast. Furthermore, the DNA fragment includes nucleotides having the sequence of SEQ. ID. NO.: 4 within a conserved domain of the chloroplast PPO protein coding sequence and base G37 of SEQ. ID. NO.: 4 is substituted by A (thus GTG→ATG) in the DNA fragment isolated from the RS-3 mutant, so that Val13 of SEQ. ID. NO.: 1 is changed to Met in the herbicide-resistant PPO protein.

As described below, there are several methods for altering the sequence of the DNA fragment encoding a protein or part of a protein having PPO activity so that the protein becomes herbicide-resistant in a manner similar to the PPO protein encoded in the DNA fragments isolated from the RS-3 mutant of *Chlamydomonas*. For example, an amino acid alteration equivalent to that found in the herbicide-resistant PPO in the RS-3 mutant may be created artificially by site-directed mutagenesis methods, according to the gapped duplex method described by Kramer & Frits (*Methods in Enzymol.* 154: 350 (1987)) or according to the methods described by Kunkel (*Proc. Natl. Acad. Sci. U.S.A.* 82: 488 (1985)) or Kunkel et al., (*Methods in Enzymol.* 154: 367 (1987)), with appropriate modifications, if needed.

Alternatively, DNA fragments encoding herbicide-sensitive PPO obtained as described above may be mutagenized according to in vivo mutagenesis methods, (e.g. Miller, *Experiments in Molecular Genetics*, c. 1990 by Cold Spring Harbor Laboratory, Cold Spring Harbor, N.Y. or Sherman et al., *Methods in Yeast Genetics*, c. 1983 by Cold Spring Harbor Laboratory, Cold Spring Harbor, N.Y.). Standard in vitro mutagenesis methods can also be used (e.g. Shortie et al., *Methods in Enzmmol.* 100: 457 (1983); Kadonaga et al., *Nucleic Acid Research*, 13: 1733 (1985); Hutchinson et al., *Proc. Natl. Acad. Sci. U.S.A.* 83: 710 (1986); Shortie et al., *Proc. Natl. Acad. Sci. U.S.A.* 79: 1588 (1982) or Shiraishi et al., (*Gene* 64: 313 (1988)). The mutagenized fragment comprising the amino acid alteration equivalent to the RS-3 mutation may be isolated and examined to see whether it confers PPO herbicide resistance in vivo. To examine the PPO-inhibiting herbicide resistance of the mutagenized gene, herbicide-sensitive cells such as those of wild type *Chlamydomonas reinhardtii* may be transformed with the mutagenized PPO genes by standard methods to see if PPO-inhibiting herbicide resistance is conferred by the mutagenized PPO gene.

The herbicide-resistant PPO gene thus obtained can be introduced into plant or algal cells by itself or in the form of a chimeric DNA construct. A promoter that is active in plants may be operably fused to the herbicide resistance PPO gene in the chimeric DNA construct. Examples of promoters capable of functioning in plants or plant cells, i.e., those capable of driving expression of associated structural genes such as PPO in plant cells, include the cauliflower mosaic virus (CaMV) 19S or 35S promoters and CaMV double promoters (Mitsuhara et al., *Plant Cell Physiol.* 37: 49 (1996), the nopaline synthase promoter (Fraley et al., *Proc. Natl. Acad. Sci. U.S.A.* 80: 4803 (1983)); pathogen related (PR) protein promoters (Somssich, "Plant Promoters and Transcription Factors", pp. 163-179 in *Results and Problems in Cell Differentiation*, Vol. 20, Nover, ed., c. 1994 by Springer-Verlag, Berlin, 1994); the promoter for the gene encoding the small subunit of ribulose bisphosphate carboxylase (ssuRUBISCO) (Broglie et al., *Biotechnology* 1:55 (1983)), the rice actin promoter (McElroy et al., *Mol. Gen. Genet.* 231: 150 (1991)), and the maize ubiquitin promoter (EP 0 342 926; Taylor et al., *Plant Cell Rep.* 12: 491 (1993)). Sequences encoding signal or transit peptides may be fused to the herbicide-resistant PPO coding sequence in the chimeric DNA construct to direct transport of the expressed PPO enzyme to the desired site of action. Examples of signal peptides include those linked to the plant pathogenesis-related proteins, e.g. PR-1, PR-2, and the like (see, e.g. Payne et al., *Plant Mol. Biol.* 11: 89 (1988)). Examples of transit peptides include chloroplast transit peptides such as those described in Von Heijne et al., *Plant Mol. Biol. Rep.* 9: 104 (1991); Mazur et al., *Plant Physiol.* 85: 1110 (1987); and Vorst et al., *Gene* 65: 59 (1988).

In addition, a construct may include sequences encoding markers selective for transformation. Examples of selectable markers include peptides providing herbicide, antibiotic or drug resistance, such as, for example, resistance to hygromycin (Gritz and Davies, *Gene* 25: 179 (1983)), kanamycin (Mazodier et al., *Nuc. Acid. Res.* 13: 195 (1985)), G418 (Colbere-Garapin et al., *J. Mol. Biol.* 150:1 (1981)), streptomycin (Shuy and Walter, *J. Bacteriol.* 174: 5604 (1992)), spectinomycin (Tait et al., *Gene* 36: 97 (1985)), methotrexate (Andrews et al., *Gene* 35: 217 (1985)), glyphosate (Comai et al., *Science* 221: 370 (1983)), phosphinothricin (Thompson et al., *EMBO J.* 6: 2519 (1987), DeBlock et al., *EMBO J.* 6: 2513 (1987)), or the like. These markers can be used to select for cells transformed with the chimeric DNA constructs from the background of untransformed cells. Other useful markers are peptide enzymes which can be easily detected by a visible color reaction, including luciferase (Ow et al., *Science* 234: 856 (1986)), β-glucuronidase (Jefferson et al., *Proc. Natl. Acad. Sci.* 83: 8447 (1986)), or β-galactosidase (Kalnins et al., *EMBO J.* 2: 593 (1983), Casadaban et al., *Methods Enzymol.* 100: 293 (1983)).

The herbicide-resistant PPO gene or the chimeric DNA construct including the herbicide-resistant PPO gene may be inserted into a vector capable of being transformed into the host cell and being replicated. Examples of suitable host cells include *E. coli* and yeast, or the like. Examples of suitable vectors include plasmids such as pBI101, pBI101.2, pBI101.3, pBI121 (all from Clontech, Palo Alto, Calif.), pBluescript (Stratagene, LaJolla, Calif.), pFLAG (International Biotechnologies, Inc., New Haven, Conn.), pTrcHis (Invitrogen, LaJolla, Calif.), or derivatives of these plasmids.

Plasmid vectors thus obtained, containing the herbicide-resistant PPO gene or a chimeric DNA construct, or the inserts contained in the vectors, may be introduced into plant cells by an *Agrobacterium* transfection method (JP-Koukoku-H2-58917), electroporation methods using protoplasts (JP-Kokai-S60-251887 and JP-Kokai-H5-68575), or the particle-gun method (JP-Kohyou-H5-508316 and JP-Kokai-S63-258525). The resulting transformed plant cells may be isolated and cultured, according to conventional plant cell and tissue culture methods. Herbicide-resistant plants may be regenerated from cultured cells or tissue according to known methods as described, for example, by Uchimiya (*Shokubutu Idenshi Sousa Manual—Transgeneic Shokubutu no Tsukurikata*, translation: *Plant Gene manipulation Manual—Methods for producing Transgenic Plants*, pp. 27-55, 1990, Kohdan-sha Scientific, ISBN4-06-1535137C3045).

In case that said DNA fragment or the chimeric gene including the DNA fragment or the plasmid containing the DNA fragment contains a selectable marker for transformation, transformed cells may be isolated by utilizing the marker and cells transformed for PPO-inhibiting herbicide resistance may be isolated as described above.

The ability of the herbicide-resistant PPO gene thus prepared to confer resistance to PPO-inhibiting herbicides can be examined by introducing the gene into herbicide-sensitive cells wherein the gene is expressed, for example wild type *Chlamydomonas reinhardtii* cells, by standard transformation methods. Alternatively, herbicide resistance may be determined by (1) introducing the herbicide resistant PPO gene into microorganisms lacking a PPO gene and (2) selecting transformants expressing PPO activity and growing better than untransformed cells on normal agar medium and (3) testing the activity of PPO-inhibiting herbicides added to the medium on growth of the transformants and (4) comparing herbicide tolerance of transformants rescued by the herbicide-resistant PPO gene with those rescued by a herbicide-sensitive PPO gene.

In addition, this invention embodies methods to evaluate the inhibitory effects of test compounds on protoporphyrinogen oxidase activity and methods to select among test compounds those that inhibit PPO. These methods utilize the aforementioned herbicide-resistant PPO gene or its derivatives produced by genetic engineering methods.

A method to evaluate the inhibitory effect of a compound on PPO comprises (a) culturing microorganisms in the presence of test compounds. The cultured microorganisms are "sensitive microorganisms" and "resistant microorganisms". Sensitive microorganisms express genes encoding a protein with PPO activity sensitive to PPO-inhibiting herbicide derived from higher plants, animals, microorganisms, etc. "Sensitive microorganisms" include transformants which recover growth ability following introduction of PPO-inhibiting herbicide-sensitive PPO genes into mutants lacking PPO and non-transformants having PPO-inhibiting herbicide-sensitive PPO genes. "Resistant microorganisms" have genes encoding a protein with PPO activity resistant to PPO inhibitors. The resistant microorganisms are produced as transformants which recover growth ability following introduction of DNA fragments of this invention into mutants lacking active PPO, in the presence of test compounds (for example, compounds which are classified as porphyric herbicides). The growth of both sensitive and resistant microorganisms is evaluated to determine inhibitory activities of the test compounds against PPO.

A method for selecting PPO-inhibiting herbicides comprises culturing sensitive microorganisms and resistant microorganisms that differ because the sensitive microorganisms carry a gene encoding a protein with PPO activity sensitive to PPO inhibitors. The resistant microorganisms are produced as transformants which recover growth ability following introduction of DNA fragments or their equivalents used in the method of conferring resistance of this invention into mutants lacking PPO. The sensitive and resistant microorganisms are cultured in the presence of test compounds (for example, compounds which are classified as porphyric herbicides), and the compounds are identified which inhibit growth of only sensitive microorganisms at a particular dosage and permit growth of resistant organisms.

A method for selecting herbicides that do not inhibit PPO comprises culturing a sensitive microorganism and a resistant microorganism in the presence of test compounds (for example, compounds which are classified as porphyric herbicides), and identifying the compounds which inhibit growth of both sensitive and resistant microorganisms.

Crop plants made resistant to PPO-inhibiting herbicides by the subject method, can be cultivated in the presence of PPO-inhibiting herbicides to control plants which are sensitive to these herbicides by applying effective amounts of these herbicides to inhibit growth of said plants. Examples of PPO-inhibiting herbicides to be applied are the class of herbicides having the general formula X-Q as described above and also the specifically named compound listed above.

Using specific examples, the methods to evaluate the inhibitory effect of test compounds on protoporphyrinogen oxidase (PPO) activity are explained further below.

First, a vector for expressing the introduced herbicide-sensitive PPO gene in *E. coli* under the regulation of the lacZ promoter is prepared by inserting said gene into the multiple cloning site of a commercially available plasmid vector such as pUC118. The plasmid thus prepared is introduced into, for example, a mutant strain of *E. coli* (for example, strain SASX38) lacking the PPO gene (hemG locus). The *E. coli* cells are then plated on LB agar plates with ampicillin and IPTG, and cultured for about two days to obtain herbicide-sensitive transformants which form colonies. The herbicide-sensitive PPO genes may be obtained by cloning native herbicide-sensitive genes or manipulating naturally resistant PPO genes by genetic engineering methods to produce a herbicide-sensitive PPO enzyme. The herbicide-sensitive *E. coli* transformants can be used as negative controls in a method to evaluate the inhibitory effect of test compounds on protoporphyrinogen oxidase activity. Of course, untransformed native microorganisms having herbicide-sensitive PPO genes can also be used as negative controls for this purpose.

Alternatively, a vector for expressing a herbicide-resistant PPO gene in *E. coli* under the regulation of the lacZ promoter is prepared by inserting said gene into the multiple cloning site of a commercially available plasmid vector such as pUC118. The plasmid thus prepared is introduced into, for example, a mutant strain of *E. coli* (for example, strain SASX38) lacking an active PPO gene (hemG locus). The *E. coli* cells are then plated on LB agar plates with ampicillin, IPTG and herbicide, and cultured for about two days to obtain herbicide-resistant transformants which form colonies. Said herbicide-resistant PPO genes may be obtained by cloning native herbicide-resistant genes or manipulating PPO genes by genetic engineering methods to produce a gene encoding a herbicide-resistant PPO enzyme. Examples of native herbicide-resistant PPO genes are the human PPO gene described by Nishimura et al. (*J. Biol. Chem.* 270: 8076 (1995)) and an

*E. coli* PPO gene described by Sasarman et al. (Can. J. Microbiol. 39: 1155 (1993)). The herbicide-resistant *E. coli* transformants can be used as positive control in this method to evaluate the inhibitory effect of test compounds on protoporphyrinogen oxidase activity.

Both herbicide-sensitive and resistant transformants are cultured independently on agar media such as LB agar plates containing a range of concentrations of test compounds (for example, compounds which are classified as porphyric herbicides) for about two days. Growth inhibition of both classes of transformants by test compounds can be measured by observing the effect of the test compounds on colony formation of both kinds of transformants on agar plates. Alternatively, both transformant types can be grown in liquid media containing various concentrations of test compounds, and their growth can be determined by measuring the turbidity of the culture. The inhibitory effect of test compounds on protoporphyrinogen oxidase activity can be evaluated by comparing the growth of the two kinds of transformants. PPO inhibitors are compounds which slow the growth of the sensitive transformants, but do not slow the growth of the resistant transformants.

The terms "sensitive" and "resistant" in this disclosure, when used with respect to PPO inhibitors, imply both an absolute response and relative responses in terms of growth and related phenomena. Namely, in cases when significant differences exist in the inhibitory effect of test compounds on PPO activity of a sensitive and a resistant control (for example, a significant difference exists in growth of sensitive and resistant microorganisms that were independently grown in the presence of the test compounds), it is possible to examine resistance and sensitivity of enzymes encoded by PPO genes to PPO inhibitors by applying appropriate concentrations of the PPO inhibitors in the assay method of the invention. Alternatively, the inhibitory effect of PPO inhibitors on PPO activity can be examined using two or more microorganisms carrying PPO genes which encode PPO enzymes different in their sensitivity to PPO inhibitors.

Further scope of the applicability of the present invention will become apparent from the examples provided below. It should be understood, however, that the following examples, while indicating preferred embodiments of the invention, are given by way of illustration only. Various changes and modifications of the invention will become apparent to those skilled in the art from this detailed description and such modifications should be considered to fall within the scope of the invention defined by the claims.

Example 1

Construction of an *Arabidopsis thaliana* cDNA Library

Wild type *Arabidopsis thaliana* ecotype Columbia laboratory strain (which can be obtained from the Sendai *Arabidopsis* Seed Stock Center (Department of Biology, Miyagi College of Education, Aoba-yama, Sendai 980, Japan) is grown from seed and green leaves are collected after 20 days of cultivation in a greenhouse. Five grams of collected green leaves are frozen in 10 ml of liquid nitrogen and then ground with a mortar and pestle into fine powder. After vaporizing the liquid nitrogen, RNA is extracted using a commercially available kit for RNA extraction (Extract-A-PLANT™ RNA ISOLATION KIT, Clontech.) to recover total RNA (about 1 mg) from the extract by the ethanol precipitation method. Then, a commercially available Oligo dT column (5'→3') is used to separate about 50 μg of the poly-A+ RNA fraction from the total RNA thus obtained. cDNA can be synthesized from said poly-A+ RNA fraction using commercially available cDNA synthesizing kit (cDNA Synthesis System Plus, Amersham). After ligating EcoRI adapters to the cDNA thus obtained using commercially available T4 ligase (Takara Shuzo Co., Ltd.), λgt11 (Stratagene) digested with Eco RI and a commercially available in vitro packaging kit (GIGA PACK II Gold, Stratagene) can be used to prepare a cDNA expression library in a λ phage vector.

Example 2

Screening for cDNA Clones Encoding Protoporphyrinogen Oxidase

The amplified *Arabidopsis thaliana* cDNA library obtained in Example 1 or commercially available maize cDNA library is used to transform a mutant strain of *E. coli* lacking a PPO gene (hemg locus) such as strain SASX38 which is described by Sasarman et al. (*J. Gen. Microbiol.* 113: 297 (1979)) and the cells are spread onto LB agar medium plates and incubated for two days. On agar plates, the host cells show limited growth and form minute colonies because of their hemg-phenotype (lacking the PPO gene). Colonies with restored PPO function are relatively larger due to complementation with a PPO cDNA and are easily isolated. From such SASX38 transformants, phage are harvested and the clone possessing the longest cDNA insert is selected as a PPO positive cDNA clone according to the method described by Watanabe and Sugiura (*Shokubutsu Biotechnology Jikken Manual. Cloning and Secuencing*, Translation: *Manual for Plant Biotechnology Experiments, Cloning and Sequencing*, pp. 180-189, Nouson Bunka Sha (ISBN4-931205-05 C3045) (1989)).

Example 3

Re-cloning of cDNA encoding Protoporphyrinogen Oxidase into a Plasmid Vector and Determination of Nucleotide Sequence The positive cDNA clone obtained in Example 2 is re-cloned into a plasmid vector pUC118 (Takara Shuzo Co., Ltd.) according to standard methods as described by Short et al., (*Nucleic Acids Research* 16: 7583 (1988)). The plasmid is then cleaved by EcoRI (Takara Shuzo Co., Ltd.) and the molecular size of the PPO cDNA is determined by agarose gel electrophoresis.

A series of deletions of the insert thus re-cloned into said plasmid vector may then be prepared according to standard methods as described by Vieira and Messing (*Methods in Enzymol.* 153: 3 (1987)). These deletions are used for the determination of the nucleotide sequence of the cDNA insert by the dideoxy-chain-termination method as described by Sanger et al., (*Proc. Natl. Acad. Sci. U.S.A.* 74: 5463 (1977)) using Sequenase version 2 kit (U.S. Biochemical Corp.). Alternatively, several sequencing primers are synthesized to determine entire sequence of the insert.

Example 4

Construction of *Chlamydomonas reinhardtii* Genomic DNA Library

The porphyric herbicide-resistant mutant strain (RS-3) of the unicellular alga *Chlamydomonas reinhardtii* (*Chlamydomonas* Genetics Center, strain GB-2674) was cultured mixotrophically under 200 µM m$^{-2}$ S$^{-1}$ PAR cool white fluorescent light with shaking for 5 days in TAP liquid medium at 25° C. TAP medium was composed of 7 mM NH$_4$Cl, 0.4 mM MgSO$_4$, 0.34 mM CaCl$_2$, 25 mM potassium phosphate, 0.5 mM Tris (pH 7.0), 1 ml/l Hutner trace elements, 1 ml/l glacial acetic acid (described in Harris, E. H., *The Chlamydomonas Sourcebook*, pp. 576-577, c. 1989 by Academic Press, San Diego) and also contained 0.03 µM of compound A. A six liter culture of cells in early stationary growth phase (7.6×10$^6$ cells/ml) was harvested. Cells were collected by centrifugation (8,000×g, 10 min 4° C.), resuspended in 50 ml of TEN buffer composed of 10 mM Tris-HCl$_1$, 10 mM EDTA, 150 mM NaCl, pH 8.0, recentrifuged, and resuspended again in 50 ml of TEN buffer. The cells were lysed by the addition of 5 ml of 20' (w/v) SDS, 5 ml of 20% Sarkosyl, and 4 mls of a protease solution (composed of 5 g of protease (Boehringer Mannheim No. 165921), 10 ml of 1M Tris-HCl (pH 7.5) and 0.11 g of CaCl$_2$ in a total volume of 100 ml of deionized distilled water). This cell lysate was mixed by slowly rotating it in a bottle with teflon vanes for 24 hr at 4° C. Sixty ml of phenol-CIA (phenol pre-saturated with TEN buffer and mixed well with an equal volume of a chloroform:isoamylalcohol, 24:1, v/v) were subsequently added, and the contents were rotated in the same bottle at room temperature for 1 hr.

The aqueous and phenol phases were then separated by centrifugation (15,000×g, 20 min, room temperature), the aqueous (upper) phase was recovered and gently but thoroughly mixed with 2 volumes of 95% (v/v) ethanol, and the DNA precipitated by placing the contents at −20° C. overnight. The resulting precipitate was recovered by centrifugation (1,500×g, 20 min, 4° C.) and washed once with ice-cold 70% (v/v) ethanol. Excess ethanol was removed and the DNA precipitate was dried under nitrogen flow for 5 min at room temperature.

The dried precipitate was subsequently dissolved in 60 ml of 10 mM Tris (pH 7.5), and the following were added under dim light: 8 ml of 10-fold concentrated TEN buffer, 0.4 ml of ethidium bromide solution (10 mg/ml), 9.8 ml of 10 mM Tris-HCl (pH 7.5), and 120 ml of a saturated sodium iodide (NaI) solution in TEN buffer. The contents were mixed by gently inverting the container and 25 ml were dispensed into each of 8 ultracentrifuge tubes. These were centrifuged in a Beckman 70 Ti rotor (44,000 rpm, 40 hr, 20° C.). After centrifugation, the chloroplast, mitochondrial, nuclear rDNA and nuclear genomic DNA bands of differing buoyant density were visualized by long-wave UV illumination. The lowermost, major band consisting of nuclear genomic DNA was recovered by use of a syringe with a large-gauge needle. The DNA in this band was subjected to a second ultracentrifugation under the same conditions and the purified nuclear DNA band was recovered as above.

Ethidium bromide was extracted from the solution containing the recovered nuclear DNA by adding isoamyl alcohol saturated with 1-2 volumes of TEN buffer and subsequently discarding the alcohol (upper) phase. After repeating this step three times, the nuclear DNA from which ethidium bromide had been removed was precipitated by the addition of 2.5 volumes of ice-cold ethanol. The precipitate recovered was washed twice in ice-cold 95% (v/v) ethanol, redissolved in a small volume of 10 mM Tris-HCl (pH 7.5) and stored at −20° C. An aliquot of this sample was diluted 100-fold and the concentration and purity of the DNA was quantified by measuring the absorbance at 260 nm and 280 nm.

Twenty five µg of the genomic DNA thus obtained was partially digested by reaction with 0.83 units of the restriction enzyme Sau3AI at 37° C. for 15 min in 277 µl of 10 mM Tris-HCl buffer (pH 7.5) containing 50 mM NaCl, 10 mM MgCl$_2$ and 1 mM dithiothreitol. The reaction mixture was extracted with an equal volume of phenol equilibrated with Tris buffer (pH 7.5) followed by an equal volume of chloroform. Ammonium acetate (3 M) was added to give a final concentration of 0.4 M, followed by the addition of 2 volumes of ice-cold 95% (v/v) ethanol. This solution was mixed thoroughly and a DNA precipitate was formed by storing the sample overnight at −20° C. The precipitate was recovered by centrifugation in a tabletop centrifuge (10,000 rpm, 10 min), washed in 70% (v/v) ethanol and recentrifuged. The precipitate was then resuspended in 20 µl TE buffer (composed of 10 mM Tris-HCl, 0.1 mM Na$_2$EDTA), and the DNA was dephosphorylated by the addition of 70 µl of deionized distilled water, 10 µl of 10-fold concentrated CIAP buffer (composed of 0.5M Tris-HCl (pH 8.5), 1 mM EDTA) and 1 unit of CIAP (Calf Intestinal Alkaline Phosphatase). The total volume of 100 µl was incubated for 60 min at 37° C. and the reaction halted by the addition of 3 µl 0.5 M EDTA (pH 8.0) and heat-treatment for 10 min at 68° C. The DNA was subjected to phenol and chloroform extractions and precipitated by the addition of ethanol containing ammonium acetate as described above.

The precipitate was washed with 70% (v/v) ethanol and the recovered DNA redissolved in TE buffer to a final concentration of 0.5 µg/ml. Subsequently the commercially available cosmid vector SuperCos-1 (Stratagene Inc.) was prepared following the protocol outlined in the SuperCos-1 instruction manual provided by the manufacturer. The vector was digested with the restriction enzyme XbaI, dephosphorylated with CIAP, redigested with the restriction enzyme BamHI, recovered by ethanol precipitation, and redissolved in TE buffer to a final concentration of 1 µg/ml. Prepared genomic DNA fragments (2.5 µg) were ligated to 1 µg of the prepared SuperCos-1 vector in 20 µl of reaction buffer (composed of 1 mM ATP, 50 mM Tris-HCl (pH7.5), 7 mM MgCl$_2$, 1 mM dithiothreitol) by the addition of 2 units of T4 DNA ligase and incubation at 4° C. overnight. The hybrid cosmids thus generated (0.5 µg) were then packaged into lambda phage particles capable of infecting *E. coli* by the use of an in vitro phage packaging kit (Gigapack II XL, Stratagene Inc.) following the protocol outlined in the instruction manual provided.

Lambda phage particles harboring these hybrid cosmids were then transfected into *E. coli* strain NM554 (Stratagene, Inc.) by the procedure described below, and these *E. coli* cells were allowed to form colonies on plates of LB medium (10 g/L NaCl, 10 g/L Bacto-tryptone, 5 g/L yeast extract, pH 7.5, 1.50 (w/v) agar) containing 50 µg/ml ampicillin. The transfection protocol is as follows: (1) a single colony of the *E. coli* strain NM554 was inoculated into 50 ml of medium (5 g/L NaCl, 10 g/L Bacto-tryptone, pH 7.4, 0.2% (w/v) maltose, 10 mM MgSO$_4$) and cultured by shaking vigorously overnight at 37° C., (2) cells were collected by centrifugation (4,000 rpm, 10 min, 4° C.) and resuspended in 10 mM MgSO$_4$ to an OD$_{600}$ of 0.5, (3) 25 µl of this bacterial suspension was mixed with 25 µl of a ¹⁄₂₀th dilution of the phage particle solution harboring hybrid cosmids prepared as described above. The phage were allowed to infect *E. coli* by letting the mixture stand at room temperature for 30 min. LB medium (200 µl; 10 g/L NaCl, 10 g/L Tryptone, 5 g/L yeast extract) was subsequently added and the suspension was incubated at 37° C. for 1 hr to allow for the expression of ampicillin resistance. The suspension was then plated onto plates of LB medium containing 50 µg/ml ampicillin and colonies formed following incubation at 37° C. overnight. The transformation efficiency of the ampicillin marker was 1.7±0.1×10$^5$ transformants/µg DNA. The *E. coli* colonies containing hybrid cosmids thus obtained were individually picked with sterile toothpicks and transferred into microtiter plate wells (Falcon, 24-well plates). Each well contained 0.5 ml of LB medium with 50 µg/ml ampicillin and the plates were incubated without shaking at 37° C. for 24 hr. Ten thousand and eighty individual clones were thereby isolated in 420 microtiter plates. Then 187.5 µl of medium were removed from each well and combined in pools of 8 clones each (1.5 ml total) into 1,260 microtubes. The bacteria in each microtube were pelleted by centrifugation (10,000 rpm, 5 min, room temperature) and subjected to DNA extraction. The bacteria remaining in the microtiter plates were frozen at −70° C. following the addition of an equal volume of 30% (w/v) glycerol. These plates were subsequently stored at −20° C.

Example 5

Screening of a Genomic DNA Library from *Chlamydomonas reinhardtii* by Transformation for Isolation of the PPO-Inhibiting Herbicide Resistance Gene The various experimental methods used to screen the genomic DNA library are described below (methods A, B, C).

A. DNA Extraction.

Extraction of cosmid DNA from *E. coli* harboring the genomic DNA library generated as described in Example 4, as well as extraction of the plasmid pARG7.8 (Debuchy et al., *EMBO J.* 8: 2803, (1989)) utilized as a transformation control, was performed by standard extraction methods (for example Sambrook, et al., *Molecular Cloning*, 2nd edition, pp. 1.38-1.39, c. 1989 by Cold Spring Harbor Press, Cold Spring Harbor, N.Y.). A description of the specific protocol follows.

The bacterial pellet in each microtube was thoroughly suspended in 100 µl of Solution I (composed of 50 mM glucose, 25 mM Tris-HCl (pH 8.0), 10 mM EDTA), to which 200 µl of Solution II (composed of 0.2 N NaOH, 1% (w/v) SDS) were added. Each microtube was capped, the contents gently mixed by inverting the tube 5-6 times and the tube was cooled by placing it on ice. One hundred and fifty µl of ice-cold Solution III (composed of 60 ml of 5M potassium acetate (pH 4.8), 11.5 ml of glacial acetic acid, and 28.5 ml of deionized, distilled water) were subsequently added, the contents were mixed well and the tubes cooled on ice for 5 min. The tubes were then centrifuged in a tabletop centrifuge (10,000 rpm, 2 min, 4° C.) and the supernatant recovered. An equal volume of phenol:chloroform (1:1, pH 7.5) was added to the recovered supernatant, the contents were thoroughly mixed by vortexing and the tubes were again centrifuged in a tabletop centrifuge (10,000 rpm, 2 min, 4° C.) and the supernatant recovered. After reextraction with chloroform, 900 µl of ethanol were added to the supernatant and mixed. The DNA was precipitated by cooling the tubes on ice and the precipitates were recovered by centrifugation in a tabletop centrifuge (12,000×g, 2 min, 4° C.). The precipitate was washed in 70% (w/v) ethanol and recovered again by centrifugation (12,000×g, 2 min, 4° C.). Excess ethanol was removed by opening the microtube cap and allowing the ethanol to evaporate at room temperature for 10 min. The precipitates thus recovered were redissolved in 50 µl of TE buffer (composed of 10 mM Tris-HCl (pH 7.5), 0.1 mM Na$_2$EDTA) to solubilize the DNA.

B. Transformation by the Glass Bead Method.

The glass bead transformation protocol, when employed, followed that described by Kindle (*Proc. Natl. Acad. Sci. U.S.A.* 87: 1228 (1990)). The actual protocol employed is presented below.

First, the unicellular green alga *Chlamydomonas reinhardtii* strain CC-425 (arginine auxotroph arg-2, cell wall deficient cw-15) was cultured mixotrophically for 2 days to a cell density of 1–2×10$^6$ cells/ml in TAP liquid medium (composed of 7 mM NH$_4$Cl, 0.4 mM MgSO$_4$, 0.34 mM CaCl$_2$, 25 mM potassium phosphate, 0.5 mM Tris (pH 7.0), 1 ml/l Hutner trace elements, 1 ml/l glacial acetic acid (described in Harris, *The Chlamydomonas Sourcebook*, c. 1989 by Academic Press, San Diego, Calif.)+50 µg/ml arginine. Cells were collected by centrifugation of the culture (8,000×g, 10 min, 20° C.) and resuspended in a small volume of TAP to give a final density of 2.8×10$^8$ cells/ml.

In a small sterile test tube containing 0.3 g of sterile glass beads (0.45-0.52 mm diameter), 0.3 ml of this cell suspension, 0.5-1.0 µg of plasmid or 1-2 µg of library DNA, 0.1 ml of 20% (w/v) polyethyleneglycol (PEG) were added, mixed gently, then vortexed at high speed for 15 sec using a vortex mixer. The tube was allowed to sit for 2 min and then vortexed for another 15 sec in the same manner.

The cell suspension was then plated, 0.2 ml per plate, onto 2 plates of: a) TAP medium+1.5% (w/v) agar when using the arginine auxotroph as a transformation marker, or b) TAP medium+0.1 µM compound A+50 µg/ml arginine+1.5% (w/v) agar when using resistance to porphyric herbicides as a transformation marker and allowed to form colonies under 100 µM m$^{-2}$s$^{-1}$ light.

C. Transformation by the Particle Gun Method.

The particle gun transformation protocol, when employed, followed that described by Boynton, J. E. & Gillham, N. W. (*Methods in Enzmmol.: Recombinant DNA*, Part H, 217:510 (1993) and Randolph-Anderson, B. et al., *Bio-Rad US/EG Bulletin* 2015, pp. 1-4, Bio-Rad Laboratories, 1996). The actual protocol employed is presented below.

First, the unicellular green alga *Chlamydomonas reinhardtii* strain CC-48 (arginine auxotroph arg-2) was cultured mixotrophically for 2 days in TAP liquid medium (7 mM NH$_4$Cl, 0.4 mM MgSO$_4$, 0.34 mM CaCl$_2$, 25 mM potassium phosphate, 0.5 mM Tris (pH 7.0), 1 ml/L Hutner trace elements, 1 ml/L glacial acetic acid; described in Harris, *The Chlamydomonas Sourcebook*, Academic Press, San Diego, c. 1989)+50 µg/ml arginine to a cell density of 1.5–3×10$^6$ cells/ml. Cells were collected by centrifugation of the culture (8,000×g, 10 min, 20° C.) and resuspended in a small volume of HS medium (composed of 500 mg/L NH$_4$Cl, 20 mg/L MgSO$_4$.7H$_2$O, 10 mg/L CaCl$_2$.2H$_2$O, 1,440 mg/L K$_2$HPO$_4$, 720 mg/L KH$_2$PO$_4$, 1 ml/L Hutner trace elements (described in Harris, *The Chlamydomonas Sourcebook*, c. 1989 by Academic Press, San Diego, Calif.) to a cell density of 1.14×10$^8$ cells /ml. One ml aliquots of this cell suspension were added to small test tubes already containing 1 ml of HS medium+ 0.2% agar (Difco Bacto Agar) prewarmed to 42° C. After gentle mixing, 0.7 ml aliquots of the suspension were immediately spread uniformly onto two plates of HSHA agar medium (composed of 500 mg/L NH$_4$Cl, 20 mg/L, MgSO$_4$.7H$_2$O, 10 mg/L CaCl$_2$.2H$_2$O, 1,440 mg/L K$_2$HPO$_4$, 720 mg/L KH$_2$PO$_4$, 2.4 g/L anhydrous sodium acetate, and 1 ml/L Hutner trace elements (described in Harris, *The Chlamydomonas Sourcebook*, c. 1989 by Academic Press, San Diego, Calif.) also containing 50 µg/µl ampicillin and the cells were affixed to the surface of the plates by drying them in the dark.

Next 60 mg of gold particles (0.6 cm diameter) and 1 ml of ethanol were added to a microtube and vortexed at the highest speed for 2 minutes using a vortex mixer. The gold particles were subsequently recovered by centrifugation (10,000 rpm, 1 min., room temperature) and this washing procedure was repeated 3 times. The recovered gold particles were subsequently resuspended in 1 ml of sterile distilled water. The particles were again recovered by the same centrifugation procedure, and this washing procedure was repeated twice. Finally the gold particles were resuspended in 1 ml of sterile distilled water. Fifty μl of this particle suspension were added to a microtube, to which 5 μl of DNA (2 μg/μl), 50 μl of 2.5M CaCl$_2$ and 20 μl of 0.1M spermidine (free base) were added sequentially while agitating the tube with a vortex mixer. Mixing was continued for 3 min after which the precipitate was recovered by centrifugation (10,000 rpm, 10 sec at room temperature). The precipitated gold particles were resuspended in 250 μl ethanol, recovered again by the same centrifugation procedure and finally resuspended in 60 μl ethanol. *Chlamydomonas* cells prepared as described above were bombarded with the DNA coated gold particles thus obtained using the particle gun as described (Randolph-Anderson, B. et al., *Bio-Rad US/EG Bulletin* 2015, pp. 1-4, Bio-Rad Laboratories, 1996). Immediately afterwards, the cells were resuspended from the surface of the agar plates in 1.5 ml of HS liquid medium by scraping the surface of the plate gently with a glass rod. Half of this suspension was spread onto each of two plates of selective agar medium of the following composition: a) When employing the arginine auxotroph as a transformation marker, TAP medium+1.5% (w/v) agar was used; b) When employing resistance to porphyrin-accumulating type herbicides as a transformation marker, TAP medium+0.3 μM compound A+50 μg/ml arginine+1.5% (w/v) agar) was used. The plates were then incubated under 100 μM m$^{-2}$s$^{-1}$ light to permit colonies to form.

The experimental methods described above are used to screen the genomic DNA library. Details of the screening procedures are presented below as separate primary, secondary and tertiary screening steps.

1. Primary Screening

The unicellular green algal recipient, *Chlamydomonas reinhardtii* strain CC-425 (arginine auxotroph arg-2, cell wall defecient cw-15), was transformed with pARG 7.8 (plasmid DNA) together with the library DNA (a mixture of DNAs extracted from 48 clones) using the glass bead method (see above for details). Half of the cells in each transformation experiment (3.0×10$^7$ cells) were used to determine the transformation frequency as indicated by the arginine auxotroph phenotype. The remaining half (3.0×10$^7$ cells) were examined for acquired resistance to porphyric herbicides. This experiment was repeated 198 times, and in total, 9,504 individual clones of the library were screened. In total, 7,046 arginine prototrophs were obtained from 5.8×10$^9$ cells screened. Assuming all these arginine prototroph colonies are true transformants, the transformation frequency averaged 1.2×10$^{-6}$. Additionally, one clone was obtained that exhibited resistance to porphyric herbicides (i.e. that grew in the presence of compound A). This colony was also able to grow normally on medium lacking arginine, and exhibited a loss of motility when cultured in liquid medium.

The DNA pool of 48 clones containing the cosmid which had given rise to the colony exhibiting resistance to porphyric herbicide (cosmid clones 2953-3000) is referred to as Cos2953-Cos3000.

2. Secondary Screening.

The recipient strain of the unicellular green alga *Chlamydomonas reinhardtii* CC-48 (arginine auxotroph arg-2) was then transformed with the DNAs shown in Table 1 by the particle gun method (see above for details). Transformations with the DNA pool containing the 24 clones Cos2953-Cos2976 and the larger DNA pool Cos2953-Cos3000 both gave rise to colonies resistant to compound A as shown in Table 1, whereas no resistant transformants were obtained with the other two Cos pools and pARG 7.8. This indicates that the gene for resistance to porphyrin-accumulating type herbicides must be contained within the Cos2953Cos2976 pool.

TABLE 1

| Sample DNA | No. of colonies exhibiting arginine prototrophy (per 10$^8$ cells) | No. of colonies exhibiting resistance to compound A (per 10$^8$ cells) |
|---|---|---|
| No DNA | 0 | 0 |
| pARG 7.8 | 165 | 0 |
| pARG 7.8 Cos2953-Cos3000 | 46 | 4 |
| pARG 7.8 Cos2953-Cos2976 | 67 | 20 |
| pARG 7.8 Cos2977-Cos3000 | 40 | 0 |
| pARG 7.8 Cos5833-Cos5856 | 29 | 0 |
| pARG 7.8 Cos1033-Cos1056 | 34 | 0 |

3. Tertiary Screening.

The recipient unicellular green alga *Chlamydomonas reinhardtii* strain CC-48 (arginine auxotroph arg-2) was then transformed with hybrid cosmid DNA prepared as described from the respective clones which make up the DNA pool Cos2953-Cos2976 by the particle gun method (see above for details). Only transformation with the hybrid cosmid contained within clone Cos2955 gave rise to colonies resistant to compound A (28 colonies/1.6×10$^8$ cells transformed).

In order to confirm this result, purified hybrid cosmid DNA from Cos2955 was prepared using both a plasmid purification minicolumn method (Quiagen Inc.) and the cesium chloride density gradient centrifugation method (for example, Sambrook et al., *Molecular Cloning*, 2nd edition, pp. 1.42-1.45, c. 1989 by Cold Spring Harbor Laboratory Press, Cold Spring Harbor N.Y.). The transformation experiments were then repeated using the same protocol described above. The results showed that transformation with Cos2955 DNA reproducibly gives rise to numerous colonies (frequency, ca. 1×10$^{-6}$) exhibiting resistance to compound A, indicating that a porphyric herbicide resistance gene must be contained within this hybrid cosmid DNA.

Example 6

Isolation of the PPO Gene from a DNA Library by Hybridization

A DNA fragment comprising the nucleotide sequence of SEQ. ID. No.: 4 or parts of it can be used as a probe for isolating PPO genes from *Chlamydomonas* or plant DNA libraries according to the hybridization method described by Sambrook et al., *Molecular Cloning*, 2nd edition, pp. 1.90-1.110, c. 1989 by Cold Spring Harbor Laboratory Press, Cold Spring Harbor, N.Y.

A nitrocellulose filter is placed on a 150 mm plate containing LB-ampicillin (50 μg/ml) medium, and *E. coli* XL-Blue MR cells (Stratagene) transfected with cosmid pools of the *Chlamydomonas* genomic DNA library are spread on the nitrocellulose filters (master filters), and incubated at 37° C. overnight to produce ~5×10$^5$ colonies per plate. Each master filter is replicated and the replicas are used for hybridization with PPO gene probes. The replica filters are placed sequentially for five min each on Whatman 3MM paper soaked in denaturing solution (0.5 M NaOH, 1.5 M NaCl) to lyse the bacterial cells, in neutralizing solution (0.5 M Tris-HCl (pH7.4)), and in 2×SSC at room temperature, air dried on 3MM paper for 30 min and then baked at 80° C. under vacuum for two hours to bind the DNA to the nitrocellulose. The filters are then incubated at 42° C. for about one hour in hybridization buffer (2×PIPES buffer, 50% deionized formamide, 0.5% (w/v) SDS, 500 µg/ml denatured sonicated salmon sperm DNA), followed by hybridization in the same buffer at 42° C. overnight with labeled probes at ~1×10$^6$ cpm/ml. After washing the filters in 2×SSC, 1% (w/v) SDS, positive signals can be detected by autoradiography. For higher stringencies, the filters may be washed for 60 minutes in 300-500 ml of a solution of 0.2×SSC and 0.1% SDS at 68° C. The hybridization probes consist of DNA fragments comprising the nucleotide sequence of SEQ. ID. No.: 4, or part of it, labeled with $^{32}$P using a commercially available random priming kit for DNA labeling (Takara Shuzo Co., Ltd.) or a 5'-end labeling kit (MEGALABEL, Takara Shuzo Co., Ltd.). Colonies at positions showing positive hybridization signals are scraped from the master filter and suspended in 100 µl of LB+ampicillin (50 µg/ml) medium. After spreading 100 to 1000 cells on a nitrocellulose filter and incubating it on a plate (150 mm) of LB+ampicillin (50 µg/ml) medium at 37° C. overnight, the filter is replicated. This replica filter is then used to repeat the hybridization according to the aforementioned methods to isolate positive clones.

Example 7

Isolation and Identification of the DNA Fragment Encoding Herbicide-Resistant PPO by Subcloning and Determination of the Nucleotide Sequence 1. Construction of a Restriction Map of Cos2955.

Hybrid cosmid DNA from clone Cos2955 was purified by the CsCl density gradient centrifugation method. The purified hybrid cosmid DNA (referred to below as Cos2955 DNA) was digested with restriction enzymes EcoRI, SalI, BamHI, ClaI, XhoI, and HindIII either alone or in combination, and the sizes of the fragments thus generated were estimated by 0.8% agarose gel electrophoresis (25V, 15 hr). From an analysis of the sizes of each fragment in single and double digests, the restriction map shown in FIG. 1 was constructed. HindIII and XhoI sites were examined in the 13.8 kb and smaller fragments. PstI and PmaCI sites were examined in the 3.4 kb and the 2.6 kb fragments. Five PstI sites and one PmaCI site were located in the 3.4 kb fragment. The Cos2955 DNA insert contains sites for the following restriction enzymes (in order and with the distances (kB) between sites given in parentheses): HindIII, (0.8), SalI, (0.2), BamHI, (2.8), HindIII, (5.1), XhoI, (0.9), SalI, (0.2), SalI, (0.1), BamHI, (0.5), PstI, (0.1), PstI, (0.4), PstI, (0.1), PstI, (0.3), PmaCI, (0.2), PstI, (0.6), XhoI, (1.4), EcoRI, (3.1), ClaI, (8.2), BamHI, (6.6), BamHI (3.1), BamHI, (4.4), and ClaI. The total molecular size (nucleic acid length) of the DNA fragment inserted in Cos2955 and is approximately 40.4 kb.

2. Subcloning and Sequencing of the 2.6 kb Xho/PmaCI DNA Fragment.

Figure 2:
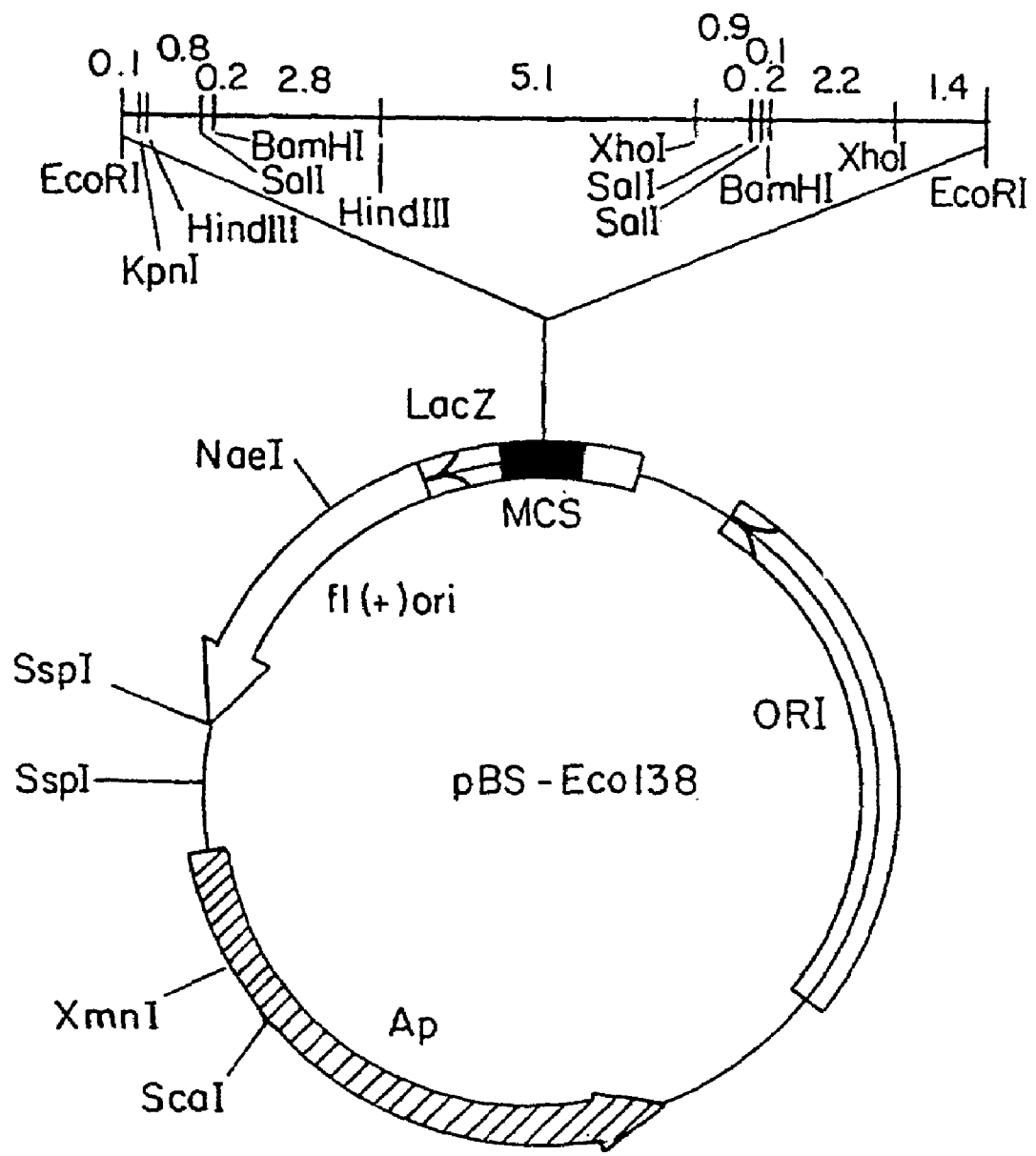
FIG. 2 diagrams the structure of a pBS plasmid having the Eco13.8 fragment of Cos2955 as the insert. Distances between restriction sites (kb) are indicated by the numbers above the insert.
Figure 3:
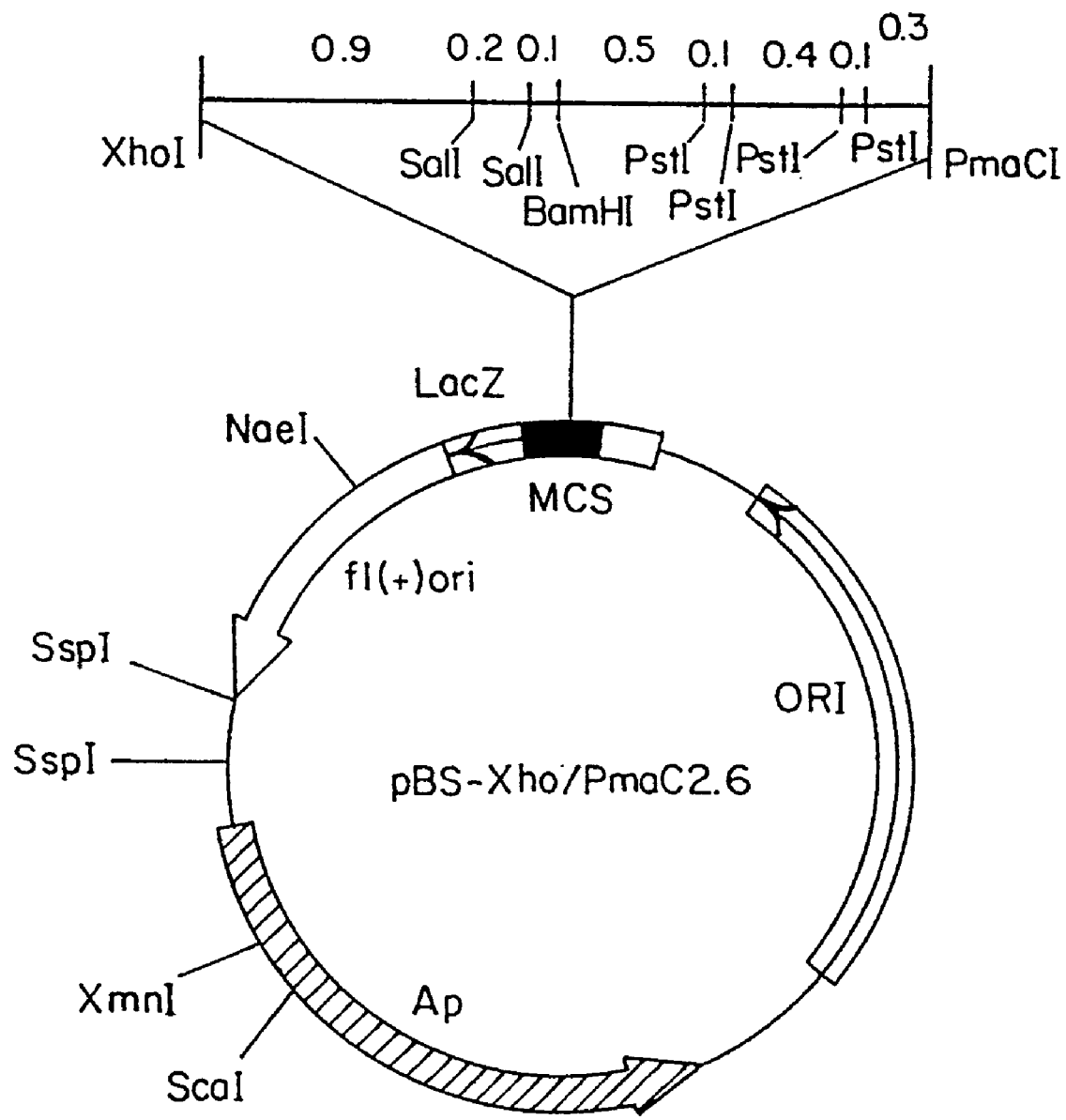
FIG. 3 illustrates the structure of a pBS plasmid having the Xho/PmaC2.6 fragment of Eco13.8 as the insert. Distances between restriction sites (kb) are indicated by the numbers above the insert.

Cos2955 DNA and the commercially-available plasmid pBluescript-II KS+ (pBS, Stratagene, Inc.) DNA were digested with individual restriction enzymes or appropriate combinations of two restriction enzymes, extracted with phenol/chloroform and the fragments were recovered by ethanol precipitation. The pBS vector was dephosphorylated by treatment with CIAP if necessary, and the pBS vector and the digested Cosmid 2955 DNA fragments were ligated using T4 DNA ligase. The hybrid plasmids thus obtained were introduced into cells of *E. coli* strain XL1-Blue by electroporation (12.5 kV/cm, 4.5 ms) and spread onto LB agar plates (composed of 10 g/L NaCl, 10 g/L Tryptone, 5 g/L yeast extract, 1.5% (w/v) agar and also containing 1 mM IPTG and 50 µg/ml ampicillin) upon which 2% (w/v) X-gal had been spread. From these plates, white colonies, i.e., those clones that had taken up the pBS vector and were thus ampicillin-resistant, and which had a DNA fragment derived from Cos2955 DNA inserted into the cloning site in the LacZ gene of the pBS vector, were isolated. The isolated colonies were cultured in the presence of ampicillin, and plasmid DNA was subsequently isolated from those colonies by the alkaline lysis method (Sambrook et al., *Molecular Cloning*, 2nd edition, Cold Spring Harbor Laboratory Press, Cold Spring Harbor N.Y., pp. 1.38-1.39 (1989). The isolated plasmids were re-digested with the restriction enzyme(s) used for cloning to release the inserts, and the sizes of the fragments obtained were again estimated by 0.8% (w/v) agarose gel (75V, 5 hr) electrophoresis. When an insert of the desired size was obtained, it was subjected to further restriction analysis in order to confirm that the correct DNA fragment had been cloned. The DNA fragments thus cloned are shown in FIG. 1. Eco13.8 DNA contains sites for the following restriction enzymes (in order and with the distances (kB) between sites given in parentheses; this same notation will be used throughout): KpnI, (<0.1), HindIII, (0.8), SalI, (0.2), BamHI, (2.8), HindIII, (5.1), XhoI, (0.9), SalI, (0.2), SalI, (0.1), BamHI, (0.5), PstI, (0.1), PstI, (0.4), PstI, (0.1), PstI, (0.3), PmaCI, (0.2), PstI, (0.6), XhoI, (1.4), and EcoRI. The total molecular size (nucleic acid length) of the Eco13.8 DNA fragment is approximately 13.8 kb. Hind10.0 DNA contains sites for the following restriction enzymes (in order and with the distances (kB) between sites given in parentheses): KpnI, (<0.1), HindIII, (5.1), XhoI, (0.9), SalI, (0.2), SalI, (0.1), BamHI, (0.5), PstI, (0.1), PstI, (0.4), PstI, (0.1), PstI, (0.3), PmaCI, (0.2), PstI, (0.6), XhoI, (1.4), and EcoRI. The total molecular size (nucleic acid length) of the Hind10.0 DNA fragment is approximately 10.0 kb. The Hind10.0 fragment is a derivative of the Eco13.8 fragment from which has been deleted a DNA fragment of approximately 3.8 kb containing sites for the restriction enzymes HindIII, (0.8), SalI, (0.2), BamHI, (2.8), HindIII. The Hind10.0 fragment was obtained by digesting the Eco13.8 fragment with HindIII and ligating the digest. Xho3.4 DNA contains sites for the following restriction enzymes (in order and with the distances (kB) between sites given in parentheses): XhoI, (0.9), SalI, (0.2), SalI, (0.1), BamHI, (0.5), PstI, (0.1), PstI, (0.4), PstI, (0.1), PstI, (0.3), PmaCI, (0.2), PstI, (0.6), and XhoI. The total molecular size (nucleic acid length) of the Xho3.4 DNA fragment is approximately 3.4 kb. Xho/PmaC2.6 DNA contains sites for the following restriction enzymes (in order and with the distances (kB) between sites given in parentheses): XhoI, (0.9), SalI, (0.2), SalI, (0.1), BamHI, (0.5), PstI, (0.1), PstI, (0.4), PstI, (0.1), PstI, (0.3) and PmaCI. The plasmid containing the Xho/PmaC2.6 fragment was obtained by digesting the pBS plasmid containing the Xho3.4 fragment with KpnI and PmaCI, blunting with T4 DNA polymerase, self ligating and transforming *E. coli*. In this process a DNA fragment of approximately 0.8 kb containing sites for the restriction enzymes XhoI, (0.6) and PstI, (0.2) was deleted. The total molecular size (nucleic acid length) of the Xho/PmaC2.6 DNA fragment is approximately 2.6 kb.

In order to identify the clone containing the porphyric herbicide resistance mutation rs-3, the recipient *Chlamydomonas reinhardtii* strain CC-48 (arginine auxotroph arg-2) was transformed with DNA from the pBS subclones of Cos2955 by the particle gun method (see above for details).

The pBS subclones of Cos2955 that were able to confer resistance to compound A contained the Eco13.8, Hind10.0, Xho3.4 and Xho/PmaC2.6 fragments. Of these fragments, the Xho/PmaC2.6 fragment had the smallest size. These results confirmed that the Xho/PmaC2.6 fragment contains the porphyric herbicide resistance mutation.

E. coli strains containing pBS plasmids with the Eco13.8 and Xho/PmaC2.6 fragments described above inserted have been deposited with the Chlamydomonas Genetics Center, c/o Dr. Elizabeth H. Harris, DCMB Group, LSRC Building, Research Drive, Box 91000, Duke University, Durham, N.C., 27708-1000 under the designation of P-563 and P-717, respectively. E. coli containing Cos2955 has also been deposited with the Chlamydomonas Genetics Center under the designation P-561. In addition, E. coli strain XL1-Blue/Eco13.8 was deposited with the American Type Culture Collection (12301 Parklawn Drive, Rockville, Md., 20852, USA) on Jul. 19, 1995, under the terms of the Budapest Treaty, and has been given the deposit designation ATCC 69870.

The nucleotide sequence of the Xho/PmaC2.6 and Xho3.4 DNA fragments obtained as described above were determined by the Sanger enzymatic sequencing method (Sequenase Version 2.0 kit, USB Inc.) using $\alpha^{35}$S-dATP or $\alpha^{32}$P-DATP label (see, SEQ. ID. No.: 10 and SEQ. ID. No.: 19).

Example 8

Isolation of Spontaneous Mutants of Chlamydomonas reinhardtii Resistant to PPO-Inhibiting Herbicides The unicellular green alga Chlamydomonas reinhardtii strain CC-125 (wild type) was cultured mixotrophically for 2 days in TAP liquid medium, as described in Example 5, to a cell density of ca. $3 \times 10^6$ cells/ml. Cells were collected by centrifugation of the culture (8,000×g, 10 min, 20° C.) and resuspended in a small volume of HS media (described in Example 5) to a cell density of $1 \times 10^8$ cells/ml. Multiple 1 ml aliquots of this cell suspension were added to small test tubes already containing 1 ml of HS media+0.2% agar (Difco Bacto Agar) prewarmed to 42° C. After gentle mixing, two 0.7 ml aliquots of the suspension were each spread onto petri plates of herbicide containing TAP agar (composed of TAP medium+0.3 µM compound A+1.5% (w/v) agar), and the cells were affixed to the surface of the plates by drying them in the dark. The plates were then incubated under 100 µM $m^{-2}s^1$ light for two weeks. Sufficient wild type cells were screened in this manner until normal green colonies were identified on some of the TAP plates containing 0.3 µM compound A. This screening procedure is also applicable for isolation of herbicide-resistant mutants from mutagenized wild type cells. A green colony from the unmutagenized wild type cells selected on TAP plates containing 0.3 µM compound A was transferred to a small volume of HS liquid medium. This cell suspension was diluted several times and spread on herbicide-containing TAP plates to obtain single colonies. A single resistant colony was re-isolated and was deposited with the Chlamydomonas Genetics Center (described in Example 7) under the designation of GB-2951.

Resistance of GB-2951 to several herbicides was tested by growing the strain in TAP liquid media containing various concentration of the compounds, according to the method described by Shibata et al. (Research in Photosynthesis, Vol III, pp. 567-570, Murata ed., c. 1992 by Kluwer Academic Publisher, Dordrecht, Netherlands). Like the RS-3 mutant GB-2674, GB-2951 showed resistance to PPO-inhibiting herbicides containing compound A and to acifluorfen-methyl, but was as sensitive to herbicides having other mechanisms of action (e.g. diuron and paraquat) as wild type strain CC-125. Moreover, GB-2951 was crossed to wild type strain CC-124 and several sets of tetrads were isolated according to the method as described by Harris (Harris, E. H., The Chlamydomonas Sourcebook, c. 1989 by Academic Press, San Diego, Calif.). All tetrads segregated two herbicide (compound A) sensitive and two herbicide-resistant progeny. In addition, tetrads from a cross of GB-2951 to RS-322, a porphyria herbicide-resistant isolate from a cross of RS-3 and CC-124, yielded no herbicide-sensitive progeny. These results indicate that GB-2951 has a single nuclear gene mutation to porphyric herbicide resistance, which has very similar characteristics to the mutation in RS-3 (designated as rs-3) and maps at or very close to the rs-3 locus.

Example 9

Isolation of the Herbicide-Sensitive PPO Gene from Wild Type Chlamydomonas reinhardtii A Chlamydomonas reinhardtii genomic DNA library is constructed from a wild type strain CC-125 according to the method as described in Example 4. Each clone may be either preserved individually in an indexed library as described in Example 4, or the library may be preserved as a population of clones as described by Sambrook et al., (Molecular Cloning 2nd edition, pp. 2.3-2.53, c. 1989 by Cold Spring Harbor Laboratory Press, Cold Spring Harbor, N.Y.). Alternatively, mRNA from wild type strain CC-125 of Chlamydomonas reinhardtii is extracted according to the method described by Rochaix et al. (Plant Molecular Biology. A Practical Approach, Shaw, ed., Chapter 10, p. 253-275 (1988)), and the cDNA library is constructed according to the method as described in Example 1. DNA fragments comprising the base sequence of SEQ. ID. NO.: 4, or part of it, such as a 1.2 kb DNA fragment obtained by digesting the Xho3.4 fragment with BamHI, can be used as probes to screen the cDNA library. Positive clones are detected and isolated according to the method as described in Example 7. The nucleotide sequence of the DNA insert in the isolated clone is determined, and compared with the SEQ. ID. NO.: 4 to confirm that the clone corresponds to the desired wild type gene.

Example 10

Analysis of the Deduced Amino Acid Sequence of the Protein Encoded by the PPO Gene Based on the known sequences of cDNA from Arabidopsis thaliana and maize (WO95/34659) (SEQ. ID. NO.: 11 and SEQ. ID. NO.: 13, respectively), amino acid sequence analysis was done on the Xho/PmaC2.6 genomic DNA from Chlamydomonas obtained in Example 7 (see SEQ. ID. NO.: 10) using the gene analysis software GENETYX (SDC Software Development). The PPO enzyme proteins encoded by the known cDNAs derived from Arabidopsis thaliana and maize consist of 537 and 483 amino acid residues, as shown in SEQ. ID. NO.: 11 and SEQ. ID. NO.: 13, respectively. Analysis of the Xho/PmaC2.6 genomic sequence from Chlamydomonas revealed the existence of four exons encoding an approximately 160 amino acid sequence homologous to the PPO protein encoded by the cDNAs derived from Arabidopsis thaliana and maize (59% and 62% identity, respectively). SEQ. ID. NO.: 1, SEQ. ID. NO.: 2 and SEQ. ID. NO.: 3 show the homologous primary amino acid sequence of the PPO protein domain encoded by part of the four Chlamy-

*domonas reinhardtii* exons and by the corresponding portions of the *Arabidopsis thaliana* and maize cDNAs. (Amino acid identity: *Chlamydomonas reinhardtii—Arabidopsis thaliana*, 57%; maize—*Chlamydomonas reinhardtii*, 60%). SEQ. ID. NO.: 4, SEQ. ID. NO.: 5 and SEQ. ID. NO.: 6 show the DNA sequences corresponding to protein SEQ. ID. NO.: 1, SEQ. ID. NO.: 2 and SEQ. ID. NO.: 3, respectively (nucleotide identity: *Chlamydomonas reinhardtii—Arabidopsis thaliana*, 51%; maize—*Chlamydomonas reinhardtii*, 54%).

Example 11

Identification of the PPO-Inhibiting Herbicide Resistance Mutation in the Herbicide-Resistant PPO Gene Genomic DNA derived from wild type strains or herbicide-resistant mutants of *Chlamydomonas reinhardtii*, or cloned DNA fragments derived from these genomes were used as templates to amplify exon domains deduced from the *Arabidopsis thaliana* cDNA sequence, using PCR methods described below that were developed for amplifying G+C rich nuclear DNA sequences from *Chlamydomonas*. The base sequences of the amplified fragments were determined, and the sequences were compared between the wild type strain and two resistant mutants.

Genomic DNA was isolated from the RS-3 (GB-2674) and RS-4 (GB-2951) strains of *C. reinhardtii* which are resistant to PPO-inhibiting herbicides and from the herbicide-sensitive wild type strains (CC-407 and CC-125) according to a method similar to that described in Example 4. The following reaction mixture (100 µl) was prepared containing 7-deaza-2'-deoxyguanosine triphosphate (7-Deaza-dGTP) (Innis, "PCR with 7-deaza-2'-deoxyguanosine triphosphate", p. 54 in *PCR Protocols, Guide to Methods and Applications*, c. 1990 by Academic Press, San Diego, Calif.). Composition of the reaction mixture was: 200 µM each DATP, dCTP, dTTP, Na or Li salts (Promega or Boehringer); 150 µM 7-Deaza-dGTP, Li salt (Boehringer); 50 µM dGTP, Na or Li salt (Promega or Boehringer); 1.5 mM magnesium acetate (Perkin-Elmer); 1×XL Buffer II (Perkin-Elmer) containing Tricine, potassium acetate, glycerol, and DMSO; 0.2 µM of each primer; ca. 500 ng of total genomic miniprep DNA. Synthetic oligonucleotides were synthesized corresponding to the intron regions flanking the 5' end of the first exon sequence and the 3' end of the second exon sequence in the Xho/PmaC2.6 fragment (SEQ. ID. NO.: 10) for use as primers: Primer 1A ($^{167}$CCGTC TACCA GTTT CTTG$^{184}$; SEQ. ID. NO.: 15) and primer 2B ($^{865}$TGGAT CGCTT TGCTC AG$^{849}$; SEQ. ID. NO.: 18) to amplify a 699 bp product containing exons 1 and 2. Synthetic oligonucleotides were synthesized corresponding to the intron regions flanking the 5' end of the third exon sequence in the Xho/PmaC2.6 fragment (SEQ. ID. No.: 10) and the 3' end of a fifth exon sequence present in the Xho3.4 fragment (SEQ. ID. No.: 19) for use as primers: Primer 3A (1698TTCCA CGTCT TCCAC CTG $^{1715}$; SEQ. ID. No.: 20) and primer 5B ($^{2782}$CGGCA TTTAC CAGCT AC$^{2766}$; SEQ. ID. No.: 24) to amplify a 1085 bp product containing exons 3, 4 and 5.

Three units of rTth DNA polymerase XL (Perkin-Elmer) were added to the reaction mixtures in the thermocycler after the temperature reached 90° C. PCR products were amplified under the following conditions: 93° C. 3 min (1 cycle); 93° C. 1 min, 47° C. 1 min, 72° C. 3 min, extended 1 sec per cycle (35 cycles); 72° C. 10 min (1 cycle). The reaction products were analyzed on 0.8% agarose gels, purified by isopropanol precipitation and sequenced using the dsDNA cycle sequencing system (GIBCO-BRL) using the following primers, which were ended labeled using $^{32}$P or $^{33}$P gamma ATP (NEN): Exon 1 was sequenced from the 1A/2B PCR product using primers 1A (see above) and 1B ($^{506}$ATACA ACCGC GGGAT ACGA$^{488}$; SEQ. ID. NO.: 16); exon 2 was sequenced from the 1A/2B PCR product using primers 2A ($^{577}$ACTTT GTCTG GTGCT CC$^{593}$; SEQ. ID. NO.: 17) and 2B (see above). The DNA sequence of exon 1 of the wild type strains (CC-407 and CC-125) was obtained (SEQ. ID. NO.: 4). The comparable base sequences of the RS-3 (GB-2674) and RS-4 (GB-2951) mutant strains were found to have an identical G→A change from wild type to mutant at bp position 37 in SEQ. ID. NO.: 4 which corresponds to bp 1108 in the *Arabidopsis* PROTOX gene (SEQ. ID. No.: 11). This results in a Val→Met substitution at Val13 in wild type *C. reinhardtii*, which corresponds to Val365 in the *Arabidopsis* PROTOX gene (SEQ. ID. No.: 11). Both the wild type and the mutant nucleotide sequences of the other exons in the Xho/PmaC2.6 fragment were determined by essentially the same method as described above. Exon 2 was sequenced from the 1A/2B PCR product using primers 2A ($^{577}$ACTTT GTCTG GTGCT CC$^{593}$; SEQ. ID. No.: 17) and 2B (see above); exon 3 was sequenced from the 3A/5B PCR product using primers 3A (see above) and 3B ($^{1914}$CTAGG ATCTA GCCCA TC$^{1898}$; SEQ. ID. No.: 21); and exon 4 was sequenced from the 3A/5B PCR product using primers 4A ($^{2122}$CTGCA TGTGT AACCC CTC$^{2139}$; SEQ. ID. No.: 22) AND 4B ($^{2416}$GACCT CTTGT TCATG CTG$^{2399}$; SEQ. ID. No.: 23). In each case the mutant and wild type sequences were found to be identical.

Example 12

Creation of Herbicide-Resistant PPO Genes by Site Directed Mutagenesis

Conventional site-directed mutagenesis methods such as the gapped-duplex method described by Kramer et al. (*Nucleic Acids Research* 12: 9441 (1984)) or Kramer and Frits (*Methods in Enzymol.* 154: 350 (1987)) can be used to introduce base substitutions into the herbicide-sensitive plant PPO gene such that the protein produced by said modified gene exhibits resistance to PPO-inhibiting herbicides. Synthetic oligonucleotides are designed so that Val13 (in SEQ. ID. NO.: 1) is substituted by Met in the exon encoding the amino acid of SEQ. ID. NO.: 1 in the PPO gene.

For example, the positive clone obtained in Example 2 is re-cloned into the phage vector M13 ty19 (Takara Shuzo Co., Ltd.) so that the protein encoded by said clone can be expressed according to the method described by Short et al., (*Nucleic Acids Research* 16: 7583 (1988)). Said phage vector is used as a template and a commercially available site-directed mutagenesis system kit (Mutan-G, Takara Shuzo Co., Ltd.) is employed. The 5'-ends of synthetic oligonucleotides corresponding to parts of the SEQ. ID. NO.: 7 (for *Arabidopsis thaliana* cDNA), SEQ. ID. NO.: 8 (for maize cDNA) or SEQ. ID. NO.: 9 (common to both) are phosphorylated with a commercially available kit (MEGALABEL, Takara Shuzo Co., Ltd.) and then used to prime oligonucleotide synthesis on the complementary strand of gapped-duplex phage DNA to introduce said herbicide resistance mutation. DNA with the complementary mutant strand synthesized in vitro is introduced into *E. coli* BMH71-18 (mutS) (Takara Shuzo Co., Ltd.) according to standard methods as described by Hanahan (*J. Mol. Biol.* 166: 557 (1983)), Sambrook et al., (*Molecular Cloning*, 2nd edition, pp. 1.74-1.84 and pp. 4.37-4.38, c. 1989 by Cold Spring Harbor Laboratory Press, Cold Spring Harbor, N.Y.). The phage are then plated for plaque formation on *E. coli* MV1184 (Takara Shuzo Co., Ltd.). Single-stranded DNA is prepared from the plaques thus formed according to standard methods as described by Sambrook et al., (*Molecular Cloning*, 2nd edition, p. 4.29, c. 1989 by Cold Spring Harbor Laboratory Press, Cold Spring Harbor, N.Y.), and the base sequence of the cDNA domain is determined using a Sequenase version 2 kit (U.S. Biochemical Corp.) according to the dideoxy-chain-termination method as described by Sanger et al., (*Proc. Natl. Acad.Sci. U.S.A.* 74: 5463 (1977)). Clones are then selected which have the base sequence of the synthetic oligonucleotide used for mutagenesis.

Example 13

Evaluation of Inhibitory Effects of Test Compounds on PPO Activity and Identification of new PPO Inhibitors The plasmid vector containing the cDNA encoding a herbicide-sensitive PPO enzyme obtained in Example 2 or 9 is introduced into the mutant SASX38 strain of *E. coli* in which the endogenous the PPO gene (hemG locus) is deleted and herbicide-sensitive transformants are selected by the method in Example 2. Similarly, a cDNA encoding a herbicide-resistant PPO is obtained according to the method in Example 12, with a base pair alteration at the position of Val13 in SEQ. ID. NO.: 1, SEQ. ID. NO.: 2 and SEQ. ID. NO.: 3 resulting in the substitution of methionine for valine. Said cDNA is re-cloned in the plasmid vector pUC118 (Nishimura et al., *J. Biol. Chem.* 270: 8076 (1995)), and said plasmid vector is introduced into *E. coli* SASX38 to obtain herbicide-resistant transformants. Both sensitive and resistant transformants are separately plated on LB+ ampicillin agar medium supplemented with compound A at a given concentration, and incubated for two days. Colony formation is then evaluated to assess the growth of the sensitive and resistant transformants in the presence of the herbicide. Growth of *E. coli* strains with the cDNA encoding a herbicide-sensitive PPO (sensitive transformants) is strongly suppressed on LB+ampicillin medium containing a particular concentration of Compound A compared to that in medium lacking Compound A. In contrast, *E. coli* strains with a cDNA encoding a herbicide-resistant PPO (resistant transformants) show the same level of growth in both of medium supplemented with Compound A at that concentration and medium free of Compound A. Therefore, the growth inhibition of said sensitive transformants relative to said resistant transformants, which differ genetically only by a base pair substitution in their PPO genes, is caused by the inhibitory effect of the compound on the PPO enzyme. Identification of new compounds with PPO inhibitory activity (test compounds) as well as the determination of the relative effectiveness of previously identified PPO inhibitors is accomplished by adding them to the medium of the aforementioned *E. coli* transformants with sensitive and resistant PPO genes and comparing the effects of these compounds on the relative growth rates of said sensitive and resistant transformants.

Example 14

Construction of an Expression Vector Containing a PPO Gene for Electroporation and Particle Gun Transformation An expression vector for direct introduction of the PPO gene into plants or plant tissue culture cells is described in this example. From plasmids pWDC-4 or pWDC-3 (WO95/134659) containing the known maize PPO cDNAs (MzProtox-1 or MzProtox-2), the ~1.75 kb or 2.1 kb fragment corresponding to the PPO coding sequence is excised using commercially available restriction enzymes according to conventional engineering methods as described by Sambrook et al., (*Molecular Cloning*, 2nd edition, Cold Spring Harbor Laboratory Press, Cold Spring Harbor, N.Y., p. 5.3-6.3 (1989)). According to the method of Example 12, the termini of the resulting fragments are blunt ended using T4 DNA polymerase (DNA blunting kit, Takara Shuzo Co., Ltd.).

Separately, the pUC19-derived GUS expression vector pBI221 (Clontech) is digested with restriction enzymes SmaI and SacI (Takara Shuzo Co., Ltd.) to recover a 2.8 Kbp fragment with the GUS coding sequences excised and having the CaMV 35S promoter and the NOS terminator at opposite ends. The termini of this fragment are also blunt ended using T4 DNA polymerase (Takara Shuzo Co., Ltd.) and dephosphorylated with bacterial alkaline phosphatase (Takara Shuzo Co., Ltd.).

Blunt ended fragments of said cDNA and said vector are fused using T4 DNA ligase (DNA ligation kit: Takara Shuzo Co., Ltd.) and transformed into competent cells of *E. coli* strain HB101 (Takara Shuzo Co., Ltd.). Ampicillin resistant clones are selected, and plasmid DNAs are isolated and characterized by restriction analysis using standard methods. Plasmid clones in which the PPO coding sequence is inserted in correct direction relative to the CaMV 35S promoter and NOS terminator are selected as expression vectors for direct introduction of the PPO gene into plants and plant cells.

Example 15

Construction of a PPO Expression Vector for *Agrobacterium*-Mediated Transformation Construction of an expression vector containing a PPO gene for *Agrobacterium* mediated transformation of plants or plant cells is described below. DNA fragments comprising PPO cDNA coding sequence can be prepared with blunted termini as described in Example 14. The binary pBIN19-derived GUS expression vector pBI121 (Clontech) is digested with restriction enzymes SmaI and SacI (Takara Shuzo Co., Ltd.) to excise the GUS coding sequence. The terminal CaMV35S promoter and NOS terminator sequences of the digested plasmid DNA are blunt ended using T4 DNA polymerase (DNA blunting kit: Takara Shuzo Co., Ltd.) and subsequently dephosphorylated with bacterial alkaline phosphatase. Following ligation of the blunt ended cDNA and vector fragments, the chimeric plasmid is introduced into competent cells of *E. coli* strain HB101 (Takara Shuzo Co., Ltd.) and clones with the recombinant plasmid are selected on LB medium containing 50 µg/ml kanamycin. Restriction analysis of plasmid DNA isolated from these clones is done using standard methods to identify those clones in which the PPO coding sequence is inserted in the correct orientation for expression. The selected PPO expression vector is then introduced into *Agrobacterium tumefaciens* strain LBA 4404 by the tri-parental mating method (GUS gene fusion system, Clontech).

Example 16

Production of Transgenic Crop Plants Transformed with the PPO Gene Expression Vector

*Agrobacterium tumefaciens* LBA4404 into which the PPO gene expression vector in Example 15 has been introduced is used to infect sterile cultured leaf sections of tobacco or other susceptible plant tissues according to the method described by Uchimiya (*Shokubutsu Idenshi Sousa Manual*, translation: *Plant Genetic Engineering Manual*, pp. 27-33, Kodansha Scientific (ISBN4-06-153513-7) (1990)) to obtain transformed tobacco plants. Transformed calli are selected on MS-NB medium plates (Murashige & Skoog medium+0.1 mg/l naphthaleneacetic acid+1.0 mg/l benzyl adenine, 0.8% agar) containing 50 µg/ml kanamycin and plantlet formation is induced by transfer of the resistant calli onto Murashige & Skoog medium plates containing 50 µg/ml kanamycin. Similarly, sterile petioles of cultured carrot seedlings are infected with the aforementioned *Agrobacterium* strain carrying the PPO expression vector according to the method described by Pawlicki et. al. (*Plant Cell, Tissue and Organ Culture* 31:129 (1992)) to obtain transformed carrot plants after regeneration.

Example 17

Weed Control Tests Involving Application of PPO-Inhibiting Herbicides on Mixtures of Weeds and Herbicide-Resistant Crop Plants Flats with an area of 33×23 cm² and a depth of 11 cm are filled with upland field soil. Seeds of crop plants with herbicide-resistant PPO genes developed according to methods similar to those described in Example 16 are planted along with those of weeds such as *Echinochloa crus-galli*, *Abutilon theophrasti* and *Ipomoea hederacea*, and covered with 1-2 cm soil. Compounds of formulae 20 and 22 (wherein R is an ethyl group) of an amount of equivalent to 100 g/ha are dissolved in 20 volumes of a mixture of surfactant and liquid carrier, such as a mixture of calcium dodecylbenzenesulfonate/polyoxyethylene styrylphenyl ether/xylene/cyclohexanone=1:2:4:8 (v/v), and diluted with water of a volume equivalent to 10 L/ha, then sprayed on surface of the soil immediately after sowing. Test plants are grown in a greenhouse for 27 days after treatment to observe weed control activity and crop phytotoxicity of the test compounds.

Seeds of the aforementioned crop plants with herbicide-resistant PPO genes are planted along with those of weeds such as *Echinochloa crus-galli*, *Abutilon theophrasti* and *Ipomoea hederacea*, covered with soil of 1-2 cm deep, and the plants grown for 18 days in the greenhouse. Compounds of formulae 20 and 22 (wherein R is an ethyl group) of an amount of equivalent to 100 g/ha are dissolved in 20 volumes of a mixture of surfactant and liquid carrier, such as the mixture of calcium dodecylbenzenesulfonate/polyoxyethylene styrylphenyl ether/xylene/cyclohexanone=1:2:4:8 (v/v), and diluted with water of a volume equivalent to 10 L/ha, then sprayed onto plants from the above. Test plants are grown in a greenhouse for 20 days after treatment for observation of weed control activity and crop phytotoxicity by test compounds.

In either method, no significant phytotoxicity is observed in the crop plants transformed with the herbicide-resistant PPO gene, while growth of *Echinochloa crus-galli*, *Abutilon theophrasti* and *Ipomoea hederacea* is inhibited.

Various modifications of the invention described herein will become apparent to those skilled in the art. Such modifications are intended to fall within the scope of the appended claims.

SEQUENCE LISTING

```
<160> NUMBER OF SEQ ID NOS: 24

<210> SEQ ID NO 1
<211> LENGTH: 47
<212> TYPE: PRT
<213> ORGANISM: Chlamydomonas reinhardtii
<220> FEATURE:
<221> NAME/KEY: misc_feature
<223> OTHER INFORMATION: Strain CC-407
<221> NAME/KEY: PEPTIDE
<222> LOCATION: (1)..(47)
<223> OTHER INFORMATION: product = porphyric herbicide resistance domain

<400> SEQUENCE: 1

Ala Ala Glu Ala Leu Gly Ser Phe Asp Tyr Pro Pro Val Gly Ala Val
1               5                   10                  15

Thr Leu Ser Tyr Pro Leu Ser Ala Val Arg Glu Glu Arg Lys Ala Ser
            20                  25                  30

Asp Gly Ser Val Pro Gly Phe Gly Gln Leu His Pro Arg Thr Gln
        35                  40                  45

<210> SEQ ID NO 2
<211> LENGTH: 46
<212> TYPE: PRT
<213> ORGANISM: Arabidopsis thaliana
<220> FEATURE:
<221> NAME/KEY: misc_feature
<223> OTHER INFORMATION: ecotype Columbia
<221> NAME/KEY: PEPTIDE
<222> LOCATION: (1)..(46)
<223> OTHER INFORMATION: product = porphyric herbicide resistance domain
```

-continued

```
<400> SEQUENCE: 2

Ala Ala Asn Ala Leu Ser Lys Leu Tyr Tyr Pro Pro Val Ala Ala Val
1               5                   10                  15

Ser Ile Ser Tyr Pro Lys Glu Ala Ile Arg Thr Glu Cys Leu Ile Asp
            20                  25                  30

Gly Glu Leu Lys Gly Phe Gly Gln Leu His Pro Arg Thr Gln
        35                  40                  45

<210> SEQ ID NO 3
<211> LENGTH: 46
<212> TYPE: PRT
<213> ORGANISM: Zea mays
<220> FEATURE:
<221> NAME/KEY: misc_feature
<223> OTHER INFORMATION: Strain B73 inbred
<221> NAME/KEY: PEPTIDE
<222> LOCATION: (1)..(46)
<223> OTHER INFORMATION: product = porphyric herbicide resistance domain

<400> SEQUENCE: 3

Ala Ala Asp Ala Leu Ser Arg Phe Tyr Tyr Pro Pro Val Ala Ala Val
1               5                   10                  15

Thr Val Ser Tyr Pro Lys Glu Ala Ile Arg Lys Glu Cys Leu Ile Asp
            20                  25                  30

Gly Glu Leu Gln Gly Phe Gly Gln Leu His Pro Arg Ser Gln
        35                  40                  45

<210> SEQ ID NO 4
<211> LENGTH: 141
<212> TYPE: DNA
<213> ORGANISM: Chlamydomonas reinhardtii
<220> FEATURE:
<221> NAME/KEY: misc_feature
<223> OTHER INFORMATION: Strain CC-407
<221> NAME/KEY: misc_feature
<222> LOCATION: (1)..(141)
<223> OTHER INFORMATION: encodes porphyric herbicide resistance domain

<400> SEQUENCE: 4
gccgccgagg ccctgggctc cttcgactac ccgccggtgg gcgccgtgac gctgtcgtac      60
ccgctgagcg ccgtgcggga ggagcgcaag gcctcggacg ggtccgtgcc gggcttcggt     120
cagctgcacc cgcgcacgca g                                               141

<210> SEQ ID NO 5
<211> LENGTH: 138
<212> TYPE: DNA
<213> ORGANISM: Arabidopsis thaliana
<220> FEATURE:
<221> NAME/KEY: misc_feature
<223> OTHER INFORMATION: ecotype Columbia
<221> NAME/KEY: misc_feature
<222> LOCATION: (1)..(138)
<223> OTHER INFORMATION: encodes porphyric herbicide resistance domain

<400> SEQUENCE: 5
gctgcaaatg cactctcaaa actatattac ccaccagttg cagcagtatc tatctcgtac       60
ccgaaagaag caatccgaac agaatgtttg atagatggtg aactaaaggg ttttgggcaa     120
ttgcatccac gcacgcaa                                                   138

<210> SEQ ID NO 6
<211> LENGTH: 138
<212> TYPE: DNA
<213> ORGANISM: Zea mays
```

```
<220> FEATURE:
<221> NAME/KEY: misc_feature
<223> OTHER INFORMATION: Strain B73 inbred
<221> NAME/KEY: misc_feature
<222> LOCATION: (1)..(138)
<223> OTHER INFORMATION: encodes porphyric herbicide resistance domain

<400> SEQUENCE: 6
gctgcagatg ctctatcaag attctattat ccaccggttg ctgctgtaac tgtttcgtat      60
ccaaaggaag caattagaaa agaatgctta attgatgggg aactccaggg ctttggccag     120
ttgcatccac gtagtcaa                                                   138

<210> SEQ ID NO 7
<211> LENGTH: 36
<212> TYPE: DNA
<213> ORGANISM: Artificial Sequence
<220> FEATURE:
<221> NAME/KEY: misc_feature
<222> LOCATION: (1)..(36)
<223> OTHER INFORMATION: Oligonucleotide primer for Arabidopsis thaliana

<400> SEQUENCE: 7
ctatattacc caccaatggc agcagtatct atctcg                                36

<210> SEQ ID NO 8
<211> LENGTH: 38
<212> TYPE: DNA
<213> ORGANISM: Artificial Sequence
<220> FEATURE:
<221> NAME/KEY: misc_feature
<222> LOCATION: (1)..(38)
<223> OTHER INFORMATION: Oligonucleotide primer for Zea mays

<400> SEQUENCE: 8
gattctatta tccaccgatg gctgctgtaa ctgtttcg                              38

<210> SEQ ID NO 9
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: Oligonucleotide primer common to both of A.
      thaliana and Z. mays porphyric herbicide resistance domain of PP
<221> NAME/KEY: misc_feature
<222> LOCATION: (1)..(26)
<223> OTHER INFORMATION: "n" residues can be inosine in addition to G,
      A, T or C; "k" at position 1 is equal to G or T; "y" at positions
      3 and 6 is equal to C or T; "s" at positions 17 and 26 is equal to
      C or G; and "w" at position 25 is equal to A or T

<400> SEQUENCE: 9
kaytayccnc cnatggsngc ngtnws                                           26

<210> SEQ ID NO 10
<211> LENGTH: 2573
<212> TYPE: DNA
<213> ORGANISM: Chlamydomonas reinhardtii
<220> FEATURE:
<221> NAME/KEY: misc_feature
<223> OTHER INFORMATION: Strain RS-3
<221> NAME/KEY: misc_feature
<222> LOCATION: (1)..(2573)
<223> OTHER INFORMATION: encodes protoporphyrinogen oxidase
```

```
<400> SEQUENCE: 10
ctcgagagcg ttggaggaaa tccgtttggc acctgttccg gcttctttgt gtgcacggcc      60
acgtccccct ttcctgctac ccgctccccc ccggctttac tgccccttcc actcctcggc     120
tccatcccga ttccatccgc tcctcctccc ccacctagac tgtctaccgt ctaccagttt     180
cttgggcaat cattaacgta accccgcctc cctgcgcctg cccctccctc cctctccccc     240
ccgcacagcc cgccgccgcc gaggccctgg gctccttcga ctacccgccg atgggcgccg     300
tgacgctgtc gtacccgctg agcgccgtgc gggaggagcg caaggcctcg acgggtccg      360
tgccgggctt cggtcagctg cacccgcgca cgcaggtggg caagtgcgcg cgtgttgcgg     420
gcggtgtgtt gcggagggga gggtggtggg ggttgggggt ggggtgggg gggattgggg      480
cgctgggtcg tatcccgcgg ttgtatcctc gcgctcccct catccattcc cccttcaac     540
aacacacacg ggcgcacacg caccctcttt gcgcttactt tgtctggtgc tccttaacac     600
actcttcgct tcattttggt gtcttctaac acacacactt gtccacacac agggcatcac     660
cactctgggc accatctaca gctccagcct gttccccggc cgcgcgcccg agggccacat     720
gctgctgctc aactacatcg gcggcaccac caaccgcggc atcgtcaacc agaccaccga     780
gcagctggtg gagcaggtgt gtgtgtgggg gggtgggggg ggggcagtgg attttttgggc    840
tgagcccct gagcaaagcg atccagggg ggcgaagccc cccaggattg ccctgtccg       900
tgcgtgcgtg tgtgcctgtg tcgacaaaaa gtaccgtact ggcacaaacc gcgagtgcca     960
cgtattatta attgcaatta cctattgtag aaaaatagac ggcagggaaa actcggccgg    1020
agcgagaagc gacctcgtga gtccatggac atcttgactt tcttcagttc gcgagtatag    1080
ctctcggccc ctaaatatct tacatccatg tatcaaaaca tgtcgacgac aagcgtcttg    1140
gggcaagaat gtcgaaattg tttgcaacag ccaaaccatg cgtccccgag ccttacatgt    1200
gtcgcggccc gggatcccgc gcccgagccc ggctagccct ttgcggtgct tgagtgggat    1260
gtgggtgagg tgcatttggg atatcatgga ccgtgaagtg gcgtgggtaa ggtggcgtgg    1320
cgtggcgggg acagggcatg tcggtgcctc ggcacagcgt tggcctagtg gccagtcccg    1380
ctggatgggc ttgcaagggt gctgttcatg tcgccggtgc ccatcgtcac atcccccttgc   1440
gctacatggg gctcagccca tttttccagct gtacaaagct gacacccctt gttgtgtggc   1500
gtcttggacc cgtgttgctt cggagctggc cagaaccccc tgtgggcaca cacacgcaca    1560
cacacacaca cacacacaca cacacacaca cacacacaca cacacacaca cacacacaca    1620
cacacacaca cacacacaca cacacacaca cacacacaca cacattttcg tcctgcagcc    1680
ccgaaccccg ccgcccgttc cacgtcttcc acctgccgca ccccccccc tgccgcacgc     1740
ctgctctcac cgcctctccc cccaccccat ctccctgcag gtggacaagg acctgcgcaa    1800
catggtcatc aagcccgacg cgcccaagcc ccgtgtggtg ggcgtgcgcg tgtggccgcg    1860
cgccatcccg caggtgtgag ggcgcagcag ccggagggat gggctagatc ctagtttctc    1920
aaagagctct acagccctat aacctcgacc tgcgaccttc gacctgataa cctggctgcc    1980
ccctcccaac ctagccacct ctccccgat ttgggttcac tcggttgact tgcttttggg     2040
ttctggaatc aacttcacct gttgtatact ttgctgcact tctctgtacc actctttgca    2100
ttaggttcgg tttagtttgg gctgcatgtg taaccccctcc tccccgccct gccacctgca    2160
gttcaacctg ggccacctgg agcagctgga caaggcgcgc aaggcgctgg acgcggcggg    2220
gctgcagggc gtgcacctgg ggggcaacta cgtcagcgt gagcgcgtgg gcagcagcag    2280
cagcaggaag aggggagggg aggggagggg agggtacaag gaggaggttg agcaggaggt    2340
```

-continued

```
ggtgctaagg cgcaaagcaa ggcggtgttg tatcctcatt gactgaaacc gggaaaccca    2400
gcatgaacaa gaggtcaggg gactgcaagg agcggaggct acatgtatga ctaccccga     2460 cgcgggcgat gattccttga ctattgggac ctatttcgtt gggctcgggc acatgacccc    2520
cctggcccct cgctgtatg gtgcccagcc gcccagccgc ccccgccca cac             2573
```

<210> SEQ ID NO 11
<211> LENGTH: 1704
<212> TYPE: DNA
<213> ORGANISM: Arabidopsis thaliana
<220> FEATURE:
<221> NAME/KEY: misc_feature
<223> OTHER INFORMATION: ecotype Columbia
<221> NAME/KEY: CDS
<222> LOCATION: (16)..(1629)
<223> OTHER INFORMATION: product = protoporphyrinogen oxidase

<400> SEQUENCE: 11

```
ttctctgcga tttcc atg gag tta tct ctt ctc cgt ccg acg act caa tcg         51
                Met Glu Leu Ser Leu Leu Arg Pro Thr Thr Gln Ser
                1               5                   10 ctt ctt ccg tcg ttt tcg aag ccc aat ctc cga tta aat gtt tat aag          99
Leu Leu Pro Ser Phe Ser Lys Pro Asn Leu Arg Leu Asn Val Tyr Lys
        15                  20                  25 cct ctt aga ctc cgt tgt tca gtg gcc ggt gga cca acc gtc gga tct         147
Pro Leu Arg Leu Arg Cys Ser Val Ala Gly Gly Pro Thr Val Gly Ser
    30                  35                  40 tca aaa atc gaa ggc gga gga ggc acc acc atc acg acg gat tgt gtg        195
Ser Lys Ile Glu Gly Gly Gly Gly Thr Thr Ile Thr Thr Asp Cys Val
45                  50                  55                  60 att gtc ggc gga ggt att agt ggt ctt tgc atc gct cag gcg ctt gct        243
Ile Val Gly Gly Gly Ile Ser Gly Leu Cys Ile Ala Gln Ala Leu Ala
                65                  70                  75 act aag cat cct gat gct gct ccg aat tta att gtg acc gag gct aag        291
Thr Lys His Pro Asp Ala Ala Pro Asn Leu Ile Val Thr Glu Ala Lys
            80                  85                  90 gat cgt gtt gga ggc aac att atc act cgt gaa gag aat ggt ttt ctc        339
Asp Arg Val Gly Gly Asn Ile Ile Thr Arg Glu Glu Asn Gly Phe Leu
        95                  100                 105 tgg gaa gaa ggt ccc aat agt ttt caa ccg tct gat cct atg ctc act        387
Trp Glu Glu Gly Pro Asn Ser Phe Gln Pro Ser Asp Pro Met Leu Thr
    110                 115                 120 atg gtg gta gat agt ggt ttg aag gat gat ttg gtg ttg gga gat cct        435
Met Val Val Asp Ser Gly Leu Lys Asp Asp Leu Val Leu Gly Asp Pro
125                 130                 135                 140 act gcg cca agg ttt gtg ttg tgg aat ggg aaa ttg agg ccg gtt cca        483
Thr Ala Pro Arg Phe Val Leu Trp Asn Gly Lys Leu Arg Pro Val Pro
                145                 150                 155 tcg aag cta aca gac tta ccg ttc ttt gat ttg atg agt att ggt ggg        531
Ser Lys Leu Thr Asp Leu Pro Phe Phe Asp Leu Met Ser Ile Gly Gly
            160                 165                 170 aag att aga gct ggt ttt ggt gca ctt ggc att cga ccg tca cct cca        579
Lys Ile Arg Ala Gly Phe Gly Ala Leu Gly Ile Arg Pro Ser Pro Pro
        175                 180                 185 ggt cgt gaa gaa tct gtg gag gag ttt gta cgg cgt aac ctc ggt gat        627
Gly Arg Glu Glu Ser Val Glu Glu Phe Val Arg Arg Asn Leu Gly Asp
    190                 195                 200 gag gtt ttt gag cgc ctg att gaa ccg ttt tgt tca ggt gtt tat gct        675
Glu Val Phe Glu Arg Leu Ile Glu Pro Phe Cys Ser Gly Val Tyr Ala
205                 210                 215                 220
```

```
ggt gat cct tca aaa ctg agc atg aaa gca gcg ttt ggg aag gtt tgg    723
Gly Asp Pro Ser Lys Leu Ser Met Lys Ala Ala Phe Gly Lys Val Trp
            225             230             235 aaa cta gag caa aat ggt gga agc ata ata ggt ggt act ttt aag gca    771
Lys Leu Glu Gln Asn Gly Gly Ser Ile Ile Gly Gly Thr Phe Lys Ala
        240             245             250 att cag gag agg aaa aac gct ccc aag gca gaa cga gac ccg cgc ctg    819
Ile Gln Glu Arg Lys Asn Ala Pro Lys Ala Glu Arg Asp Pro Arg Leu
    255             260             265 cca aaa cca cag ggc caa aca gtt ggt tct ttc agg aag gga ctt cga    867
Pro Lys Pro Gln Gly Gln Thr Val Gly Ser Phe Arg Lys Gly Leu Arg
270             275             280 atg ttg cca gaa gca ata tct gca aga tta ggt agc aaa gtt aag ttg    915
Met Leu Pro Glu Ala Ile Ser Ala Arg Leu Gly Ser Lys Val Lys Leu
285             290             295             300 tct tgg aag ctc tca ggt atc act aag ctg gag agc gga gga tac aac    963
Ser Trp Lys Leu Ser Gly Ile Thr Lys Leu Glu Ser Gly Gly Tyr Asn
            305             310             315 tta aca tat gag act cca gat ggt tta gtt tcc gtg cag agc aaa agt    1011
Leu Thr Tyr Glu Thr Pro Asp Gly Leu Val Ser Val Gln Ser Lys Ser
        320             325             330 gtt gta atg acg gtg cca tct cat gtt gca agt ggt ctc ttg cgc cct    1059
Val Val Met Thr Val Pro Ser His Val Ala Ser Gly Leu Leu Arg Pro
    335             340             345 ctt tct gaa tct gct gca aat gca ctc tca aaa cta tat tac cca cca    1107
Leu Ser Glu Ser Ala Ala Asn Ala Leu Ser Lys Leu Tyr Tyr Pro Pro
350             355             360 gtt gca gca gta tct atc tcg tac ccg aaa gaa gca atc cga aca gaa    1155
Val Ala Ala Val Ser Ile Ser Tyr Pro Lys Glu Ala Ile Arg Thr Glu
365             370             375             380 tgt ttg ata gat ggt gaa cta aag ggt ttt ggg caa ttg cat cca cgc    1203
Cys Leu Ile Asp Gly Glu Leu Lys Gly Phe Gly Gln Leu His Pro Arg
            385             390             395 acg caa gga gtt gaa aca tta gga act atc tac agc tcc tca ctc ttt    1251
Thr Gln Gly Val Glu Thr Leu Gly Thr Ile Tyr Ser Ser Ser Leu Phe
        400             405             410 cca aat cgc gca ccg ccc gga aga att ttg ctg ttg aac tac att ggc    1299
Pro Asn Arg Ala Pro Pro Gly Arg Ile Leu Leu Leu Asn Tyr Ile Gly
    415             420             425 ggg tct aca aac acc gga att ctg tcc aag tct gaa ggt gag tta gtg    1347
Gly Ser Thr Asn Thr Gly Ile Leu Ser Lys Ser Glu Gly Glu Leu Val
430             435             440 gaa gca gtt gac aga gat ttg agg aaa atg cta att aag cct aat tcg    1395
Glu Ala Val Asp Arg Asp Leu Arg Lys Met Leu Ile Lys Pro Asn Ser
445             450             455             460 acc gat cca ctt aaa tta gga gtt agg gta tgg cct caa gcc att cct    1443
Thr Asp Pro Leu Lys Leu Gly Val Arg Val Trp Pro Gln Ala Ile Pro
            465             470             475 cag ttt cta gtt ggt cac ttt gat atc ctt gac acg gct aaa tca tct    1491
Gln Phe Leu Val Gly His Phe Asp Ile Leu Asp Thr Ala Lys Ser Ser
        480             485             490 cta acg tct tcg ggc tac gaa ggg cta ttt ttg ggt ggc aat tac gtc    1539
Leu Thr Ser Ser Gly Tyr Glu Gly Leu Phe Leu Gly Gly Asn Tyr Val
    495             500             505 gct ggt gta gcc tta ggc cgg tgt gta gaa ggc gca tat gaa acc gcg    1587
Ala Gly Val Ala Leu Gly Arg Cys Val Glu Gly Ala Tyr Glu Thr Ala
510             515             520 att gag gtc aac aac ttc atg tca cgg tac gct tac aag taa            1629
Ile Glu Val Asn Asn Phe Met Ser Arg Tyr Ala Tyr Lys
525             530             535
```

```
atgtaaaaca ttaaatctcc cagcttgcgt gagttttatt aaatatttg agatatccaa    1689 aaaaaaaaaa aaaaa                                                    1704
```

<210> SEQ ID NO 12
<211> LENGTH: 537
<212> TYPE: PRT
<213> ORGANISM: Arabidopsis thaliana
<220> FEATURE:
<221> NAME/KEY: misc_feature
<223> OTHER INFORMATION: ecotype Columbia

<400> SEQUENCE: 12

```
Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
                20                  25                  30

Arg Cys Ser Val Ala Gly Gly Pro Thr Val Gly Ser Ser Lys Ile Glu
            35                  40                  45

Gly Gly Gly Gly Thr Thr Ile Thr Thr Asp Cys Val Ile Val Gly Gly
    50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
                85                  90                  95

Gly Asn Ile Ile Thr Arg Glu Glu Asn Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Leu Gly Ile Arg Pro Ser Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ser
    210                 215                 220

Lys Leu Ser Met Lys Ala Ala Phe Gly Lys Val Trp Lys Leu Glu Gln
225                 230                 235                 240

Asn Gly Gly Ser Ile Ile Gly Gly Thr Phe Lys Ala Ile Gln Glu Arg
                245                 250                 255

Lys Asn Ala Pro Lys Ala Glu Arg Asp Pro Arg Leu Pro Lys Pro Gln
            260                 265                 270

Gly Gln Thr Val Gly Ser Phe Arg Lys Gly Leu Arg Met Leu Pro Glu
        275                 280                 285

Ala Ile Ser Ala Arg Leu Gly Ser Lys Val Lys Leu Ser Trp Lys Leu
    290                 295                 300

Ser Gly Ile Thr Lys Leu Glu Ser Gly Gly Tyr Asn Leu Thr Tyr Glu
305                 310                 315                 320

Thr Pro Asp Gly Leu Val Ser Val Gln Ser Lys Ser Val Val Met Thr
                325                 330                 335
```

-continued

```
Val Pro Ser His Val Ala Ser Gly Leu Leu Arg Pro Leu Ser Glu Ser
            340                 345                 350

Ala Ala Asn Ala Leu Ser Lys Leu Tyr Tyr Pro Pro Val Ala Ala Val
        355                 360                 365

Ser Ile Ser Tyr Pro Lys Glu Ala Ile Arg Thr Glu Cys Leu Ile Asp
    370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Leu Phe Pro Asn Arg Ala
                405                 410                 415

Pro Pro Gly Arg Ile Leu Leu Leu Asn Tyr Ile Gly Ser Thr Asn
            420                 425                 430

Thr Gly Ile Leu Ser Lys Ser Glu Gly Glu Leu Val Glu Ala Val Asp
        435                 440                 445

Arg Asp Leu Arg Lys Met Leu Ile Lys Pro Asn Ser Thr Asp Pro Leu
    450                 455                 460

Lys Leu Gly Val Arg Val Trp Pro Gln Ala Ile Pro Gln Phe Leu Val
465                 470                 475                 480

Gly His Phe Asp Ile Leu Asp Thr Ala Lys Ser Ser Leu Thr Ser Ser
                485                 490                 495

Gly Tyr Glu Gly Leu Phe Leu Gly Gly Asn Tyr Val Ala Gly Val Ala
            500                 505                 510

Leu Gly Arg Cys Val Glu Gly Ala Tyr Glu Thr Ala Ile Glu Val Asn
        515                 520                 525

Asn Phe Met Ser Arg Tyr Ala Tyr Lys
    530                 535
```

```
<210> SEQ ID NO 13
<211> LENGTH: 1698
<212> TYPE: DNA
<213> ORGANISM: Zea mays
<220> FEATURE:
<221> NAME/KEY: misc_feature
<223> OTHER INFORMATION: Strain B73 inbred
<221> NAME/KEY: CDS
<222> LOCATION: (2)..(1453)
<223> OTHER INFORMATION: product = protoporphyrinogen oxidase

<400> SEQUENCE: 13 g aat tcg gcg gac tgc gtc gtg gtg ggc gga ggc atc agt ggc ctc tgc        49
  Asn Ser Ala Asp Cys Val Val Val Gly Gly Gly Ile Ser Gly Leu Cys
  1               5                  10                  15 acc gcg cag gcg ctg gcc acg cgg cac ggc gtc ggg gac gtg ctt gtc        97
Thr Ala Gln Ala Leu Ala Thr Arg His Gly Val Gly Asp Val Leu Val
            20                  25                  30 acg gag gcc cgc gcc cgc ccc ggc ggc aac att acc acc gtc gag cgc       145
Thr Glu Ala Arg Ala Arg Pro Gly Gly Asn Ile Thr Thr Val Glu Arg
        35                  40                  45 ccc gag gaa ggg tac ctc tgg gag gag ggt ccc aac agc ttc cag ccc       193
Pro Glu Glu Gly Tyr Leu Trp Glu Glu Gly Pro Asn Ser Phe Gln Pro
    50                  55                  60 tcc gac ccc gtt ctc acc atg gcc gtg gac agc gga ctg aag gat gac       241
Ser Asp Pro Val Leu Thr Met Ala Val Asp Ser Gly Leu Lys Asp Asp
65                  70                  75                  80 ttg gtt ttt ggg gac cca aac gcg ccg cgt ttc gtg ctg tgg gag ggg       289
Leu Val Phe Gly Asp Pro Asn Ala Pro Arg Phe Val Leu Trp Glu Gly
                85                  90                  95
```

```
aag ctg agg ccc gtg cca tcc aag ccc gcc gac ctc ccg ttc ttc gat      337
Lys Leu Arg Pro Val Pro Ser Lys Pro Ala Asp Leu Pro Phe Phe Asp
            100                 105                 110 ctc atg agc atc cca ggg aag ctc agg gcc ggt cta ggc gcg ctt ggc      385
Leu Met Ser Ile Pro Gly Lys Leu Arg Ala Gly Leu Gly Ala Leu Gly
        115                 120                 125 atc cgc ccg cct cct cca ggc cgc gaa gag tca gtg gag gag ttc gtg      433
Ile Arg Pro Pro Pro Pro Gly Arg Glu Glu Ser Val Glu Glu Phe Val
    130                 135                 140 cgc cgc aac ctc ggt gct gag gtc ttt gag cgc ctc att gag cct ttc      481
Arg Arg Asn Leu Gly Ala Glu Val Phe Glu Arg Leu Ile Glu Pro Phe
145                 150                 155                 160 tgc tca ggt gtc tat gct ggt gat cct tct aag ctc agc atg aag gct      529
Cys Ser Gly Val Tyr Ala Gly Asp Pro Ser Lys Leu Ser Met Lys Ala
                165                 170                 175 gca ttt ggg aag gtt tgg cgg ttg gaa gaa act gga ggt agt att att      577
Ala Phe Gly Lys Val Trp Arg Leu Glu Glu Thr Gly Gly Ser Ile Ile
            180                 185                 190 ggt gga acc atc aag aca att cag gag agg agc aag aat cca aaa cca      625
Gly Gly Thr Ile Lys Thr Ile Gln Glu Arg Ser Lys Asn Pro Lys Pro
        195                 200                 205 ccg agg gat gcc cgc ctt ccg aag cca aaa ggg cag aca gtt gca tct      673
Pro Arg Asp Ala Arg Leu Pro Lys Pro Lys Gly Gln Thr Val Ala Ser
    210                 215                 220 ttc agg aag ggt ctt gcc atg ctt cca aat gcc att aca tcc agc ttg      721
Phe Arg Lys Gly Leu Ala Met Leu Pro Asn Ala Ile Thr Ser Ser Leu
225                 230                 235                 240 ggt agt aaa gtc aaa cta tca tgg aaa ctc acg agc att aca aaa tca      769
Gly Ser Lys Val Lys Leu Ser Trp Lys Leu Thr Ser Ile Thr Lys Ser
                245                 250                 255 gat gac aag gga tat gtt ttg gag tat gaa acg cca gaa ggg gtt gtt      817
Asp Asp Lys Gly Tyr Val Leu Glu Tyr Glu Thr Pro Glu Gly Val Val
            260                 265                 270 tcg gtg cag gct aaa agt gtt atc atg act att cca tca tat gtt gct      865
Ser Val Gln Ala Lys Ser Val Ile Met Thr Ile Pro Ser Tyr Val Ala
        275                 280                 285 agc aac att ttg cgt cca ctt tca agc gat gct gca gat gct cta tca      913
Ser Asn Ile Leu Arg Pro Leu Ser Ser Asp Ala Ala Asp Ala Leu Ser
    290                 295                 300 aga ttc tat tat cca ccg gtt gct gct gta act gtt tcg tat cca aag      961
Arg Phe Tyr Tyr Pro Pro Val Ala Ala Val Thr Val Ser Tyr Pro Lys
305                 310                 315                 320 gaa gca att aga aaa gaa tgc tta att gat ggg gaa ctc cag ggc ttt     1009
Glu Ala Ile Arg Lys Glu Cys Leu Ile Asp Gly Glu Leu Gln Gly Phe
                325                 330                 335 ggc cag ttg cat cca cgt agt caa gga gtt gag aca tta gga aca ata     1057
Gly Gln Leu His Pro Arg Ser Gln Gly Val Glu Thr Leu Gly Thr Ile
            340                 345                 350 tac agt tcc tca ctc ttt cca aat cgt gct cct gac ggt agg gtg tta     1105
Tyr Ser Ser Ser Leu Phe Pro Asn Arg Ala Pro Asp Gly Arg Val Leu
        355                 360                 365 ctt cta aac tac ata gga ggt gct aca aac aca gga att gtt tcc aag     1153
Leu Leu Asn Tyr Ile Gly Gly Ala Thr Asn Thr Gly Ile Val Ser Lys
    370                 375                 380 act gaa agt gag ctg gtc gaa gca gtt gac cgt gac ctc cga aaa atg     1201
Thr Glu Ser Glu Leu Val Glu Ala Val Asp Arg Asp Leu Arg Lys Met
385                 390                 395                 400 ctt ata aat tct aca gca gtg gac cct tta gtc ctt ggt gtt cga gtt     1249
Leu Ile Asn Ser Thr Ala Val Asp Pro Leu Val Leu Gly Val Arg Val
                405                 410                 415
```

```
tgg cca caa gcc ata cct cag ttc ctg gta gga cat ctt gat ctt ctg    1297
Trp Pro Gln Ala Ile Pro Gln Phe Leu Val Gly His Leu Asp Leu Leu
            420                 425                 430 gaa gcc gca aaa gct gcc ctg gac cga ggt ggc tac gat ggg ctg ttc    1345
Glu Ala Ala Lys Ala Ala Leu Asp Arg Gly Gly Tyr Asp Gly Leu Phe
            435                 440                 445 cta gga ggg aac tat gtt gca gga gtt gcc ctg ggc aga tgc gtt gag    1393
Leu Gly Gly Asn Tyr Val Ala Gly Val Ala Leu Gly Arg Cys Val Glu
    450                 455                 460 ggc gcg tat gaa agt gcc tcg caa ata tct gac ttc ttg acc aag tat    1441
Gly Ala Tyr Glu Ser Ala Ser Gln Ile Ser Asp Phe Leu Thr Lys Tyr
465                 470                 475                 480 gcc tac aag tga tgaaagaagt ggagcgctac ttgccaatcg tttatgttgc        1493
Ala Tyr Lys atagatgagg tgcctccggg gaaaaaaaag cttgaatagt atttttatt cttattttgt   1553 aaattgcatt tctgttcttt tttctatcag taattagtta tattttagtt ctgtaggaga  1613 tgttctgtt cactgccctt caaaagaaat tttatttttc attcttttat gagagctgtg   1673
ctacttaaaa aaaaaaaaaa aaaaa                                        1698
```

<210> SEQ ID NO 14
<211> LENGTH: 483
<212> TYPE: PRT
<213> ORGANISM: Zea mays
<220> FEATURE:
<221> NAME/KEY: misc_feature
<223> OTHER INFORMATION: Strain B73 inbred
<400> SEQUENCE: 14

```
Asn Ser Ala Asp Cys Val Val Gly Gly Gly Ile Ser Gly Leu Cys
1               5                   10                  15

Thr Ala Gln Ala Leu Ala Thr Arg His Gly Val Gly Asp Val Leu Val
            20                  25                  30

Thr Glu Ala Arg Ala Arg Pro Gly Gly Asn Ile Thr Thr Val Glu Arg
        35                  40                  45

Pro Glu Glu Gly Tyr Leu Trp Glu Glu Gly Pro Asn Ser Phe Gln Pro
    50                  55                  60

Ser Asp Pro Val Leu Thr Met Ala Val Asp Ser Gly Leu Lys Asp Asp
65                  70                  75                  80

Leu Val Phe Gly Asp Pro Asn Ala Pro Arg Phe Val Leu Trp Glu Gly
                85                  90                  95

Lys Leu Arg Pro Val Pro Ser Lys Pro Ala Asp Leu Pro Phe Phe Asp
            100                 105                 110

Leu Met Ser Ile Pro Gly Lys Leu Arg Ala Gly Leu Gly Ala Leu Gly
        115                 120                 125

Ile Arg Pro Pro Pro Gly Arg Glu Glu Ser Val Glu Glu Phe Val
    130                 135                 140

Arg Arg Asn Leu Gly Ala Glu Val Phe Glu Arg Leu Ile Glu Pro Phe
145                 150                 155                 160

Cys Ser Gly Val Tyr Ala Gly Asp Pro Ser Lys Leu Ser Met Lys Ala
                165                 170                 175

Ala Phe Gly Lys Val Trp Arg Leu Glu Glu Thr Gly Gly Ser Ile Ile
            180                 185                 190

Gly Gly Thr Ile Lys Thr Ile Gln Glu Arg Ser Lys Asn Pro Lys Pro
        195                 200                 205

Pro Arg Asp Ala Arg Leu Pro Lys Pro Lys Gly Gln Thr Val Ala Ser
    210                 215                 220
```

```
Phe Arg Lys Gly Leu Ala Met Leu Pro Asn Ala Ile Thr Ser Ser Leu
225                 230                 235                 240

Gly Ser Lys Val Lys Leu Ser Trp Lys Leu Thr Ser Ile Thr Lys Ser
                245                 250                 255

Asp Asp Lys Gly Tyr Val Leu Glu Tyr Glu Thr Pro Glu Gly Val Val
            260                 265                 270

Ser Val Gln Ala Lys Ser Val Ile Met Thr Ile Pro Ser Tyr Val Ala
        275                 280                 285

Ser Asn Ile Leu Arg Pro Leu Ser Ser Asp Ala Ala Asp Ala Leu Ser
    290                 295                 300

Arg Phe Tyr Tyr Pro Val Ala Ala Val Thr Val Ser Tyr Pro Lys
305                 310                 315                 320

Glu Ala Ile Arg Lys Glu Cys Leu Ile Asp Gly Glu Leu Gln Gly Phe
                325                 330                 335

Gly Gln Leu His Pro Arg Ser Gln Gly Val Glu Thr Leu Gly Thr Ile
            340                 345                 350

Tyr Ser Ser Ser Leu Phe Pro Asn Arg Ala Pro Asp Gly Arg Val Leu
        355                 360                 365

Leu Leu Asn Tyr Ile Gly Gly Ala Thr Asn Thr Gly Ile Val Ser Lys
    370                 375                 380

Thr Glu Ser Glu Leu Val Glu Ala Val Asp Arg Asp Leu Arg Lys Met
385                 390                 395                 400

Leu Ile Asn Ser Thr Ala Val Asp Pro Leu Val Leu Gly Val Arg Val
                405                 410                 415

Trp Pro Gln Ala Ile Pro Gln Phe Leu Val Gly His Leu Asp Leu Leu
            420                 425                 430

Glu Ala Ala Lys Ala Ala Leu Asp Arg Gly Gly Tyr Asp Gly Leu Phe
        435                 440                 445

Leu Gly Gly Asn Tyr Val Ala Gly Val Ala Leu Gly Arg Cys Val Glu
    450                 455                 460

Gly Ala Tyr Glu Ser Ala Ser Gln Ile Ser Asp Phe Leu Thr Lys Tyr
465                 470                 475                 480

Ala Tyr Lys

<210> SEQ ID NO 15
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Oligonucleotide primer 1A for Chlamydomonas
      reinhardtii

<400> SEQUENCE: 15
ccgtctacca gtttcttg                                                  18

<210> SEQ ID NO 16
<211> LENGTH: 19
<212> TYPE: DNA
<213> ORGANISM: Artificial Sequence
<220> FEATURE:
<221> NAME/KEY: misc_feature
<222> LOCATION: (1)..(19)
<223> OTHER INFORMATION: Oligonucleotide primer 1B for Chlamydomonas
      reinhardtii

<400> SEQUENCE: 16
atacaaccgc gggatacga                                                 19
```

```
<210> SEQ ID NO 17
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Oligonucleotide primer 2A for Chlamydomonas
      reinhardtii

<400> SEQUENCE: 17
actttgtctg gtgctcc                                                  17

<210> SEQ ID NO 18
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Oligonucleotide primer 2B for Chlamydomonas
      reinhardtii

<400> SEQUENCE: 18
tggatcgctt tgctcag                                                  17

<210> SEQ ID NO 19
<211> LENGTH: 3381
<212> TYPE: DNA
<213> ORGANISM: Chlamydomonas reinhardtii
<220> FEATURE:
<221> NAME/KEY: misc_feature
<223> OTHER INFORMATION: Strain RS-3
<221> NAME/KEY: misc_feature
<222> LOCATION: (1)..(3381)
<223> OTHER INFORMATION: encodes protoporphyrinogen oxidase

<400> SEQUENCE: 19
ctcgagagcg ttggaggaaa tccgtttggc acctgttccg gcttctttgt gtgcacggcc    60
acgtccccct ttcctgctac ccgctccccc ccggctttac tgccccttcc actcctcggc   120
tccatcccga ttccatccgc tcctcctccc ccacctagac tgtctaccgt ctaccagttt   180
cttgggcaat cattaacgta acccgcctc cctgcgcctg cccctccctc cctctccccc    240
ccgcacagcc cgccgccgcc gaggccctgg gctccttcga ctaccgccg atgggcgccg    300 tgacgctgtc gtacccgctg agcgccgtgc gggaggagcg caaggcctcg gacgggtccg   360
tgccgggctt cggtcagctg cacccgcgca cgcaggtggg caagtgcgcg cgtgttgcgg   420
gcggtgtgtt gcggagggga gggtggtggg ggttgggggt ggggtgggg gggattgggg    480 cgctgggtcg tatcccgcgg ttgtatcctc gcgctcccct catccattcc cccttcaac    540 aacacacacg ggcgcacacg cacctctttt gcgcttactt tgtctggtgc tccttaacac   600
actcttcgct tcattttggt gtcttctaac acacacactt gtccacacac agggcatcac   660
cactctgggc accatctaca gctccagcct gttccccggc cgcgcgcccg agggccacat   720
gctgctgctc aactacatcg gcggcaccac caaccgcggc atcgtcaacc agaccaccga   780
gcagctggtg gagcaggtgt gtgtgtgggg ggtgggggg ggggcagtgg attttgggc    840 tgagcccct gagcaaagcg atccagggg ggcgaagccc cccaggattg ccctgtccg     900 tgcgtgcgtg tgtgcctgtg tcgacaaaaa gtaccgtact ggcacaaacc gcgagtgcca   960
cgtattatta attgcaatta cctattgtag aaaaatagac ggcagggaaa actcggccga  1020
agcgagaagc gacctcgtga gtccatggac atcttgactt tcttcagttc gcgagtatag  1080
```

```
ctctcggccc ctaaatatct tacatccatg tatcaaaaca tgtcgacgac aagcgtcttg   1140
gggcaagaat gtcgaaattg tttgcaacag ccaaaccatg cgtccccgag ccttacatgt   1200
gtcgcggccc gggatcccgc gcccgagccc ggctagccct ttgcggtgct tgagtgggat   1260
gtgggtgagg tgcatttggg atatcatgga ccgtgaagtg cgtgggtaa ggtggcgtgg    1320 cgtggcgggg acagggcatg tcggtgcctc ggcacagcgt tggcctagtg gccagtcccg   1380
ctggatgggc ttgcaagggt gctgttcatg tcgccggtgc ccatcgtcac atccccttgc   1440
gctacatggg gctcagccca ttttccagct gtacaaagct gacacccctt gttgtgtggc   1500
gtcttggacc cgtgttgctt cggagctggc cagaaccccc tgtgggcaca cacacgcaca   1560
cacacacaca cacacacaca cacacacaca cacacacaca cacacacaca cacacacaca   1620
cacacacaca cacacacaca cacacacaca cacacacaca cacattttcg tcctgcagcc   1680
ccgaaccccg ccgcccgttc cacgtcttcc acctgccgca ccccccccc tgccgcacgc   1740 ctgctctcac cgcctctccc cccacccat ctccctgcag gtggacaagg acctgcgcaa    1800
catggtcatc aagcccgacg cgcccaagcc ccgtgtggtg ggcgtgcgcg tgtggccgcg   1860
cgccatcccg caggtgtgag ggcgcagcag ccggagggat gggctagatc ctagtttctc   1920
aaagagctct acagccctat aacctcgacc tgcgaccttc gacctgataa cctggctgcc   1980
ccctcccaac ctagccacct ctcccggat ttgggttcac tcggttgact tgcttttggg     2040
ttctggaatc aacttcacct gttgtatact ttgctgcact tctctgtacc actctttgca   2100
ttaggttcgg tttagtttgg gctgcatgtg taacccctcc tccccgccct gccacctgca   2160
gttcaacctg gccacctgg agcagctgga caaggcgcgc aaggcgctgg acgcggcggg    2220
gctgcagggc gtgcacctgg ggggcaacta cgtcagcggt gagcgcgtgg gcagcagcag   2280
cagcaggaag aggggagggg aggggagggg agggtacaag gaggaggttg agcaggaggt   2340
ggtgctaagg cgcaaagcaa ggcggtgttg tatcctcatt gactgaaacc gggaaaccca   2400
gcatgaacaa gaggtcaggg gactgcaagg agcggaggct acatgtatga ctaccccga    2460 cgcgggcgat gattccttga ctattgggac ctatttcgtt gggctcgggc acatgacccc   2520
cctggcccct tcgctgtatg gtgcccagcc gcccagccgc cccccgccca cacgtgtgcc   2580
cacgcctttg cctcatcccc aaccccctcg gcccctctcc cccctcgaac ccctgcaacc   2640
aggtgtggcc ctgggcaagg tggtggagca cggctacgag tccgcagcca acctggccaa   2700
gagcgtgtcc aaggccgcag tcaaggccta agcggctgca gcagtagcag cagcagcatc   2760
gggctgtagc tggtaaatgc cgcagtggca ccggcagcag caattggcaa gcacttgggg   2820
caagcggagt ggaggcgagg gggggctac cattggcgct tgctgggatg tgtagtaaca    2880
gttggaatgg atcggggatg tggagctagg ggttcggggg tctgccaagg acataggtgg   2940
tgctgggatg agcgatgtgg ttggtaaagc tctgtcggca ccgttatgtg cgggttaact   3000
gcactatgac gctccgttgt acagccccgt tgtgcattgt ttgcatgaag ttttggcgag   3060
agtgagttgg cgcacacgcg gggcggtttg ggggcactgt ccctcagtgt ggtcccagca   3120
tagcacagga gagacacaga actgagtgac atagactagg tctcgaagta ccttcaaaag   3180
ggggctataa attgcgaata cccggagcag ggggccagac ccaaggcatt gactgtcagt   3240
gcacaagcga aagaccaatt gcatgggttg cttccgtggt gggaagagga gggcagggga   3300
gcatcgtcag gtgtatgttg cggcttcgcc cataagtgcc atggtttcga agatgcttaa   3360
gactaacaat gccaactcga g                                              3381
```

-continued

```
<210> SEQ ID NO 20
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Oligonucleotide primer 3A for Chlamydomonas
      reinhardtii

<400> SEQUENCE: 20
ttccacgtct tccacctg                                                 18

<210> SEQ ID NO 21
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Oligonucleotide primer 3B for Chlamydomonas
      reinhardtii

<400> SEQUENCE: 21
ctaggatcta gcccatc                                                  17

<210> SEQ ID NO 22
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Oligonucleotide primer 4A for Chlamydomonas
      reinhardtii

<400> SEQUENCE: 22
ctgcatgtgt aacccctc                                                 18

<210> SEQ ID NO 23
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: Oligonucleotide primer 4B for Chlamydomonas
      reinhardtii

<400> SEQUENCE: 23
gacctcttgt tcatgctg                                                 18

<210> SEQ ID NO 24
<211> LENGTH: 17
<212> TYPE: DNA
<213> ORGANISM: Artificial Sequence
<220> FEATURE:
<221> NAME/KEY: misc_feature
<222> LOCATION: (1)..(17)
<223> OTHER INFORMATION: Oligonucleotide primer 5B for Chlamydomonas
      reinhardtii

<400> SEQUENCE: 24
cggcatttac cagctac                                                  17
```

What is claimed is:

1. A method of conferring resistance to protoporphyrinogen oxidase-inhibiting herbicides upon the green algae *Chlamydomonas* or cells thereof, comprising introducing a DNA fragment or a plasmid containing the DNA fragment into the algae or algal cells, wherein said DNA fragment has the following characteristics:

(1) said DNA fragment is 2.6 to 13.8 kb in length;

(2) said DNA fragment has a sequence that can be detected and isolated by DNA-DNA or DNA-RNA hybridization to a nucleic acid sequence that is complementary to a nucleotide sequence encoding the amino acid sequence of SEQ ID NO: 1, wherein said DNA-DNA or DNA-RNA hybridization occurs under 2×PIPES buffer, 50% deionized formamide, 0.5% (w/v) SDS, 500 µg/ml denatured sonicated salmon sperm DNA at 42° C. overnight; and said DNA fragment remains hybridized after washing in 0.2×SSC, 0.1% (w/v) SDS at 68° C.;

(3) said DNA fragment encodes an amino acid sequence in which an amino acid at a position corresponding to position 13 of SEQ ID NO:1 is an amino acid other than valine; and (4) said DNA fragment has an ability to confer resistance to protoporphyrinogen oxidase-inhibiting herbicides in cells of the green algae *Chlamydomonas* when introduced therein.

2. A method of selecting the green algae *Chlamydomonas* or cells thereof upon which resistance to protoporphyrinogen oxidase-inhibiting herbicides is conferred, which comprises:

treating a population of the algae or algal cells, upon which resistance to protoporphyrinogen oxidase-inhibiting herbicides is conferred by the method according to claim 1, with a protoporphyrinogen oxidase-inhibiting herbicide in an amount which normally blocks growth of said algae or algal cells expressing only herbicide-sensitive protoporphyrinogen oxidase.

3. An isolated DNA fragment which has the following characteristics:

(1) said DNA fragment is 2.6 to 13.8 kb in length;

(2) said DNA fragment has a sequence that can be detected and isolated by DNA-DNA or DNA-RNA hybridization to a nucleic acid sequence that is complementary to a nucleotide sequence encoding the amino acid sequence of SEQ ID NO:1, wherein said DNA-DNA or DNA-RNA hybridization occurs under 2×PIPES buffer, 50% deionized formamide, 0.5% (w/v) SDS, 500 µg/ml denatured sonicated salmon sperm DNA at 42° C. overnight; and said DNA fragment remains hybridized after washing in 0.2×SSC, 0.1% (w/v) SDS at 68° C.;

(3) said DNA fragment encodes an amino acid sequence in which an amino acid at a position corresponding to position 13 of SEQ ID NO:1 is an amino acid other than valine; and (4) said DNA fragment has an ability to confer resistance to protoporphyrinogen oxidase-inhibiting herbicides in cells of the green alga *Chlamydomonas* when introduced therein.

4. The method according to claim 1, wherein the nucleic acid sequence encoding the amino acid sequence of SEQ ID NO:1 is the nucleotide sequence of SEQ ID NO:4.

5. The method according to claim 1, wherein the amino acid at the position corresponding to position 13 of SEQ ID NO:1 is methionine.

6. The method according to claim 1, wherein said DNA fragment is 2.6 kb to 3.4 kb in length.

7. The method according to claim 1, wherein said DNA fragment is 2.6 kb to 10.0 kb in length.

8. The method according to claim 1, wherein said DNA fragment is obtained from an algal cell.

9. A green alga *Chlamydomonas* upon which resistance is conferred by the method according to claim 1.

10. The isolated DNA fragment according to claim 3, wherein said amino acid other than valine is methionine.

11. The isolated DNA fragment according to claim 3, wherein the nucleotide sequence encoding the amino acid sequence of SEQ ID NO:1 is the nucleotide sequence of SEQ ID NO: 4.

12. The isolated DNA fragment according to claim 11, wherein a nucleotide corresponding to position 37 (G37) of SEQ ID NO: 4 is a nucleotide other than guanine in the sequence of the DNA fragment.

13. The isolated DNA fragment according to claim 12, wherein said nucleotide other than guanine is adenine.

14. The isolated DNA fragment according to claim 3, wherein said DNA fragment is 2.6 kb in length.

15. A plasmid comprising the DNA fragment according to claim 3.

* * * * *